United States Patent
Nettekoven et al.

(10) Patent No.: US 8,017,773 B2
(45) Date of Patent: Sep. 13, 2011

(54) CYCLOHEXYL SULFONAMIDE DERIVATIVES

(75) Inventors: Matthias Nettekoven, Wyhlen (DE); Olivier Roche, Folgensbourg (FR)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 12/689,064

(22) Filed: Jan. 18, 2010

(65) Prior Publication Data

US 2010/0120791 A1    May 13, 2010

Related U.S. Application Data

(63) Continuation of application No. 11/654,309, filed on Jan. 16, 2007, now abandoned.

(30) Foreign Application Priority Data

Jan. 23, 2006  (EP) ..................... 06100701

(51) Int. Cl.
  *C07D 241/04*  (2006.01)
  *A61K 31/4965*  (2006.01)
(52) U.S. Cl. .................. 544/391; 514/255.01
(58) Field of Classification Search .......... 544/391; 514/255.01
See application file for complete search history.

(56) References Cited

U.S. PATENT DOCUMENTS

| | | |
|---|---|---|
| 4,598,089 A | 7/1986 | Hadvary et al. |
| 4,931,463 A | 6/1990 | Barbier et al. |
| 4,983,746 A | 1/1991 | Barbier et al. |
| 5,175,186 A | 12/1992 | Barbier et al. |
| 5,246,960 A | 9/1993 | Barbier et al. |
| 5,399,720 A | 3/1995 | Karpf et al. |
| 6,004,996 A | 12/1999 | Shah et al. |

*Primary Examiner* — Janet Andres
*Assistant Examiner* — Heidi Reese
(74) *Attorney, Agent, or Firm* — George W. Johnston; Dennis P. Tramaloni; Samuel H. Megerditchian

(57) ABSTRACT

The present invention relates to compounds of formula I

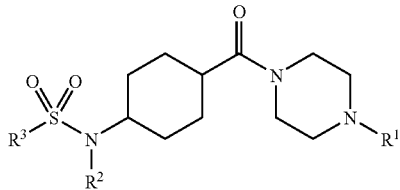

wherein $R^1$ to $R^3$ are as defined in the description and claims, and pharmaceutically acceptable salts thereof. The compounds are useful for the treatment and/or prevention of diseases which are associated with the modulation of H3 receptors.

21 Claims, No Drawings

CYCLOHEXYL SULFONAMIDE DERIVATIVES

PRIORITY TO RELATED APPLICATIONS

This application is a continuation of U.S. application Ser. No. 11/654,309, filed Jan. 16, 2007, now Pending, which claims the benefit of European Application No. 06100701.9, filed Jan. 23, 2006, which is hereby incorporated by reference in its entirety.

FIELD OF THE INVENTION

The present invention is directed to novel cyclohexyl sulfonamide derivatives, their manufacture, pharmaceutical compositions containing them and their use as medicaments. The active compounds of the present invention are useful in treating obesity and other disorders.

In particular, the present invention is directed to compounds of the general formula

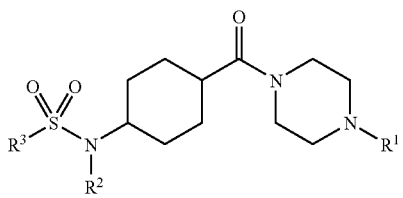

I and pharmaceutically acceptable salts thereof.

The compounds of formula I are antagonists and/or inverse agonists at the histamine 3 receptor (H3 receptor).

All documents cited or relied upon below are expressly incorporated herein by reference.

BACKGROUND

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

There is a need, therefore, for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In an embodiment of the present invention, provided is a compound of formula I:

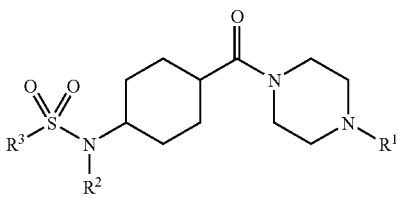

I wherein
$R^1$ is selected from the group consisting of lower alkyl, cycloalkyl, lower cycloalkylalkyl and tetrahydropyranyl;
$R^2$ is selected from the group consisting of hydrogen, lower alkyl, cycloalkyl, lower cycloalkylalkyl, lower halogenalkyl, lower alkoxyalkyl and lower cyanoalkyl;
$R^3$ is selected from the group consisting of lower alkyl, (CH$_2$)$_m$-aryl, wherein m is 0, 1 or 2 and wherein the aryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl, —(CH$_2$)$_n$-heteroaryl, wherein n is 0, 1 or 2 and wherein the heteroaryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl, and —NR$^4$R$^5$;

R$^4$ is selected from the group consisting of hydrogen, lower alkyl, lower halogenalkyl, lower alkoxyalkyl and lower cyanoalkyl;

R$^5$ is selected from the group consisting of lower alkyl, lower halogenalkyl, lower alkoxyalkyl, lower cyanoalkyl, phenyl unsubstituted or substituted with one, two or three groups independently selected from lower alkyl, halogen, lower halogenalkyl, cyano, lower alkoxy, lower alkanoyl, benzoyl, lower halogenalkoxy and lower hydroxyalkyl, and lower phenylalkyl wherein the phenyl ring may be unsubstituted or substituted with one or two groups independently selected from lower alkyl, halogen, lower halogenalkyl, cyano, lower alkoxy, lower alkanoyl, benzoyl, lower halogenalkoxy and lower hydroxyalkyl; or R$^4$ and R$^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen; and pharmaceutically acceptable salts thereof.

In another embodiment of the present invention, provided is a process for the manufacture of a compound according to formula I, comprising the steps of: reacting a compound of formula II

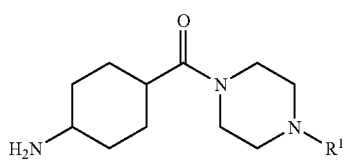

wherein R$^1$ is as defined above,
with a sulfonyl chloride of formula III

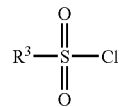

wherein R$^3$ is as defined above, in the presence of a base to obtain a compound of formula IA

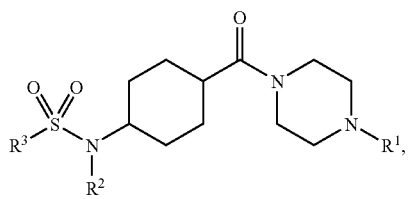

wherein R$^2$ is hydrogen, and optionally alkylating the compound of formula IA to obtain a compound of formula IB

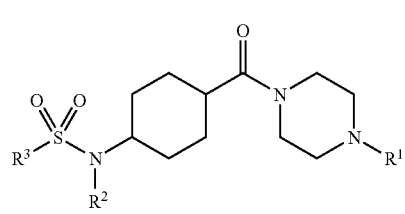

wherein R$^2$ is a group as defined above other than hydrogen, and if desired, converting the compound obtained into a pharmaceutically acceptable acid addition salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment and/or prevention of diseases which are associated with the modulation of H3 receptors, comprising the step of administering a therapeutically active amount of a compound according to formula I to a human being or animal in need thereof.

In a still further embodiment of the invention, provided is a method for the treatment or prevention of obesity in a human being or animal, comprising the step of administering to said human being or animal in need thereof a therapeutically effective amount of a compound according to formula I in combination or association with a therapeutically effective amount of a compound selected from the group consisting of a lipase inhibitor, an anorectic agent, a selective serotonin reuptake inhibitor, and an agent that stimulates metabolism of body fat.

In a yet still another embodiment of the present invention, provided is a method of treatment or prevention of type II diabetes in a human being or animal, comprising the step of administering to said human being or animal in need thereof a therapeutically effective amount of a compound of formula I in combination or association with a therapeutically effective amount of an anti-diabetic agent.

DETAILED DESCRIPTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl" or "$C_3$-$C_7$-cycloalkyl" denotes a saturated carbocyclic group containing from 3 to 7 carbon atoms, such as cyclopropyl, cyclobutyl, cyclopentyl, cyclohexyl or cycloheptyl. Especially preferred is cyclopentyl.

The term "lower cycloalkylalkyl" or "$C_3$-$C_7$-cycloalkyl-$C_1$-$C_8$-alkyl" refers to a lower alkyl group as defined above wherein at least one of the hydrogen atoms of the lower alkyl group is replaced by a cycloalkyl group, preferably cyclopropyl. Among the preferred lower cycloalkylalkyl groups is cyclopropylmethyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "halogen" refers to fluorine, chlorine, bromine and iodine, with fluorine, chlorine and bromine being preferred.

The term "lower halogenalkyl" or "halogen-$C_1$-$C_8$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, fluoromethyl and chloromethyl, with trifluoromethyl being especially preferred.

The term "lower halogenalkoxy" or "halogen-$C_1$-$C_8$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkyl" or "hydroxy-$C_1$-$C_8$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "lower cyanoalkyl" or "cyano-$C_1$-$C_8$-alkyl" refers to lower alkyl groups as defined above wherein at least one of the hydrogen atoms of the lower alkyl group is replaced by a cyano group. Examples of lower hydroxyalkyl groups are cyanomethyl or cyanoethyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "benzoyl" refers to the group —CO-phenyl, wherein the phenyl ring may be optionally substituted by one, two or three groups independently selected from the group consisting of lower alkyl, lower alkoxy, halogen, lower halogenalkyl, lower halogenalkoxy and cyano.

The term "lower alkanoylamino" or "$C_1$-$C_8$-alkanoylamino" refers to the group —NH—CO—R', wherein R' is lower alkyl and the term "lower alkyl" has the previously given significance. Preferred is a group —NH—CO—R', wherein R' is methyl, meaning acetylamino.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "aryl" refers to a monovalent aromatic carbocyclic radical consisting of one individual ring, or one or more fused rings in which at least one ring is aromatic in nature. Preferred "aryl" groups are the phenyl or naphthyl group, more preferably "aryl" refers to the phenyl group.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are pyridyl, thienyl, imidazolyl, isoxazolyl, thiazolyl and pyrazolyl.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiomorpholinyl. A preferred heterocyclyl group is piperidinyl or tetrahydropyranyl.

The term "form a 4-, 5-, 6- or 7-membered heterocyclic ring optionally containing a further heteroatom selected from nitrogen, oxygen or sulfur" refers to a N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered heterocyclic ring containing a sulfinyl group or a sulfonyl group" means a N-heterocyclic ring that contains a —S(O)— group or a —SO$_2$— group, for example 1-oxothiomorpholinyl or 1,1-dioxothiomorpholinyl. The heterocyclic ring may be unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl. The heterocyclic ring may also be condensed with a phenyl ring, said phenyl ring being unsubstituted or substituted by one, two or three groups independently selected from lower alkyl, lower alkoxy and halogen. Examples for such condensed heterocyclic rings are 3,4-dihydro-1H-isoquinoline or 1,3-dihydroisoindole.

The term "oxo" means that a C-atom of the heterocyclic ring may be substituted by =O, thus meaning that the heterocyclic ring may contain one or more carbonyl (—CO—) groups.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In more detail, the present invention relates to compounds of the general formula

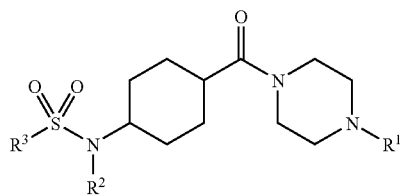

I wherein $R^1$ is selected from the group consisting of lower alkyl, cycloalkyl, lower cycloalkylalkyl and tetrahydropyranyl;

$R^2$ is selected from the group consisting of hydrogen, lower alkyl, cycloalkyl, lower cycloalkylalkyl, lower halogenalkyl, lower alkoxyalkyl and lower cyanoalkyl;

$R^3$ is selected from the group consisting of
lower alkyl,
—$(CH_2)_m$-aryl, wherein m is 0, 1 or 2 and wherein the aryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl,
—$(CH_2)_n$-heteroaryl, wherein n is 0, 1 or 2 and wherein the heteroaryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl, and —$NR^4R^5$;

$R^4$ is selected from the group consisting of hydrogen, lower alkyl, lower halogenalkyl, lower alkoxyalkyl and lower cyanoalkyl;

$R^5$ is selected from the group consisting of lower alkyl, lower halogenalkyl, lower alkoxyalkyl, lower cyanoalkyl,
phenyl unsubstituted or substituted with one, two or three groups independently selected from lower alkyl, halogen, lower halogenalkyl, cyano, lower alkoxy, lower alkanoyl, benzoyl, lower halogenalkoxy and lower hydroxyalkyl, and
lower phenylalkyl wherein the phenyl ring may be unsubstituted or substituted with one or two groups independently selected from lower alkyl, halogen, lower halogenalkyl, cyano, lower alkoxy, lower alkanoyl, benzoyl, lower halogenalkoxy and lower hydroxyalkyl; or $R^4$ and $R^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group,
said heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or
being condensed with a phenyl ring, said phenyl ring being unsubstituted or substituted by one, two or three groups independently selected from lower alkyl, lower alkoxy and halogen; and pharmaceutically acceptable salts thereof.

Preferred compounds of formula I of the present invention are compounds of formula I, wherein $R^3$ is lower alkyl.

More preferred are those compounds of formula I, wherein $R^3$ is $C_3$-$C_8$-alkyl, with those compounds of formula I, wherein $R^3$ is propyl or isopropyl, being especially preferred.

Also preferred are compounds of formula I, wherein $R^3$ is selected from the group consisting of
—$(CH_2)_m$-aryl, wherein m is 0, 1 or 2 and wherein the aryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl, and
—$(CH_2)_n$-heteroaryl, wherein n is 0, 1 or 2 and wherein the heteroaryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

Within this group, those compounds are preferred, wherein $R^3$ is —$(CH_2)_m$-aryl, wherein m is 0, 1 or 2 and wherein the aryl ring is phenyl unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

Especially preferred are those compounds of formula I, wherein $R^3$ is phenyl substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

Most preferably, $R^3$ is selected from the group consisting of 2-methylphenyl, 2,4,6-trimethylphenyl, 2-fluorophenyl, 3-fluorophenyl, 4-fluorophenyl, 4-fluoro-2-methylphenyl, 5-fluoro-2-methylphenyl, 2,4-difluorophenyl, 3,4-difluorophenyl, 3,4,5-trifluorophenyl, 3-chloro-4-fluorophenyl, 4-chloro-2-fluorophenyl, 2-chlorophenyl, 4-chlorophenyl, 2,4-dichlorophenyl, 3,4-dichlorophenyl, 2-cyanophenyl, 4-cyanophenyl, 3-cyano-4-fluorophenyl, 3-methoxyphenyl, 4-methoxyphenyl, 2,4-dimethoxyphenyl, 3,4-dimethoxyphenyl, 2,5-dimethoxyphenyl, 3-trifluoromethylphenyl, 4-trifluoromethyl-phenyl, 4-trifluoromethoxyphenyl, 4-acetylphenyl, 4-acetylaminophenyl and 4-methane-sulfonylphenyl.

A further group of preferred compounds of the present invention are the compounds of formula I, wherein $R^3$ is —$(CH_2)_n$-heteroaryl, wherein n is 0, 1 or 2 and wherein the heteroaryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

More preferably, $R^3$ is —$(CH_2)_n$-heteroaryl, wherein n is 0, 1 or 2 and wherein heteroaryl is selected from the group consisting of pyridyl, thienyl, imidazolyl, isoxazolyl, thiazolyl and pyrazolyl, said heteroaryl ring being unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl. Even more preferably, n is 0.

Especially preferred are compounds of formula I, wherein $R^3$ is heteroaryl selected from the group consisting of pyridyl, thienyl, imidazolyl, isoxazolyl, thiazolyl and pyrazolyl, said heteroaryl ring being unsubstituted or substituted with one, two or three groups independently selected from lower alkyl and halogen. Examples of such heteroaryl groups include 6-chloropyridin-3-yl, thienyl, 3,5-dimethylisoxazol-4-yl, 2,4-dimethylthiazol-5-yl, 5-chloro-thien-2-yl, 1,3-dimethyl-1H-pyrazol-4-yl, 5-bromo-6-chloro-pyridin-3-yl, 3-bromo-5-chloro-thien-2-yl, 4-bromo-5-chloro-thien-2-yl, 5-bromo-pyridin-3-yl, 2,3-dimethyl-3H-imidazol-4-yl and 5-chloro-1,3-dimethyl-1H-pyrazol-4-yl.

Especially preferred are compounds of formula I, wherein $R^3$ is pyridyl unsubstituted or substituted with halogen, preferably chloro.

Further preferred compounds are those compounds of formula I of the present invention, wherein $R^3$ is —$NR^4R^5$ and wherein $R^4$ is selected from the group consisting of hydrogen, lower alkyl, lower halogenalkyl, lower alkoxyalkyl and lower cyanoalkyl; and $R^5$ is selected from the group consisting of lower alkyl, lower halogenalkyl, lower alkoxyalkyl, lower cyanoalkyl, phenyl unsubstituted or substituted with one, two or three groups independently selected from lower alkyl, halogen, lower halogenalkyl, cyano, lower alkoxy, lower alkanoyl, benzoyl, lower halogenalkoxy and lower hydroxyalkyl, and lower phenylalkyl wherein the phenyl ring may be unsubstituted or substituted with one or two groups independently selected from lower alkyl, halogen, lower halogenalkyl, cyano, lower alkoxy, lower alkanoyl, benzoyl, lower halogenalkoxy and lower hydroxyalkyl.

Especially preferred compounds are those, wherein $R^3$ is —$NR^4R^5$ and $R^4$ and $R^5$ are lower alkyl.

Most preferably, $R^4$ and $R^5$ are methyl.

Furthermore compounds of formula I according to the present invention are preferred, wherein $R^1$ is lower alkyl or cycloalkyl.

More preferred compounds of formula I according to the invention are those, wherein $R^1$ is lower alkyl, with those compounds wherein $R^1$ is isopropyl or tent-butyl, being especially preferred.

Also preferred are compounds of formula I, wherein $R^1$ is cycloalkyl, with those compounds wherein $R^1$ is cyclopentyl or cyclobutyl being especially preferred.

Further preferred are compounds of formula I, wherein $R^1$ is lower cycloalkylalkyl or tetrahydropyranyl. Preferably, lower cycloalkylalkyl is cyclopropylmethyl.

Preferred are further compounds of formula I according to the invention, wherein $R^2$ is selected from the group consisting of hydrogen, lower alkyl and lower cycloalkylalkyl.

One group of preferred compounds of formula I are those, wherein $R^2$ is hydrogen.

Also preferred are compounds of formula I, wherein $R^2$ is lower alkyl, with those compounds, wherein $R^2$ is methyl or isopropyl being especially preferred. Most preferred $R^2$ is isopropyl.

A further group of preferred compounds of formula I according to the invention are those, wherein $R^2$ is lower cycloalkylalkyl. Especially preferred are those compounds of formula I, wherein $R^2$ is cyclopropylmethyl.

Preferred compounds of formula I of the present invention are the following:

N-{trans-4-[(4-isopropylpiperazin-1-yl)carbonyl]cyclohexyl}propane-1-sulfonamide, N-{trans-4-[(4-isopropylpiperazin-1-yl)carbonyl]cyclohexyl}propane-2-sulfonamide, N'-{trans-4-[(4-isopropylpiperazin-1-yl)carbonyl]cyclohexyl}-N,N-dimethylsulfamide, N-{trans-4-[(4-isopropylpiperazin-1-yl)carbonyl]cyclohexyl}-2-methylbenzene-sulfonamide, 2-fluoro-N-{trans-4-[(4-isopropylpiperazin-1-yl)carbonyl]cyclohexyl}benzene-sulfonamide, 4-fluoro-N-{trans-4-[(4-isopropylpiperazin-1-yl)carbonyl]cyclohexyl}benzene-sulfonamide, 4-cyano-N-{trans-4-[(4-isopropylpiperazin-1-yl)carbonyl]cyclohexyl}benzene-sulfonamide, N-{trans-4-[(4-isopropylpiperazin-1-yl)carbonyl]cyclohexyl}-4-methoxybenzene-sulfonamide, N-{trans-4-[(4-isopropylpiperazin-1-yl)carbonyl]cyclohexyl}-3-methoxybenzene-sulfonamide, 4-fluoro-N-{trans-4-[(4-isopropylpiperazin-1-yl)carbonyl]cyclohexyl}-2-methylbenzene-sulfonamide, 1-(3-fluorophenyl)-N-{trans-4-[(4-isopropylpiperazin-1-yl)carbonyl]cyclohexyl}-methanesulfonamide,
2,4-difluoro-N-{trans-4-[(4-isopropylpiperazin-1-yl)carbonyl]cyclohexyl}benzene-sulfonamide,
N-{trans-4-[(4-isopropylpiperazin-1-yl)carbonyl]cyclohexyl}-2,4,6-trimethylbenzene-sulfonamide,
3-chloro-4-fluoro-N-{trans-4-[(4-isopropylpiperazin-1-yl)carbonyl]cyclohexyl}benzene-sulfonamide,
N-{trans-4-[(4-isopropylpiperazin-1-yl)carbonyl]cyclohexyl}-2,4-dimethoxybenzene-sulfonamide,
N-{trans-4-[(4-isopropylpiperazin-1-yl)carbonyl]cyclohexyl}-2,5-dimethoxybenzene-sulfonamide,
N-{trans-4-[(4-isopropylpiperazin-1-yl)carbonyl]cyclohexyl}-3,4-dimethoxybenzene-sulfonamide,
N-{trans-4-[(4-isopropylpiperazin-1-yl)carbonyl]cyclohexyl}-4-(trifluoromethyl)benzene-sulfonamide,
2,4-dichloro-N-{trans-4-[(4-isopropylpiperazin-1-yl)carbonyl]cyclohexyl}benzene-sulfonamide,
3,4-dichloro-N-{trans-4-[(4-isopropylpiperazin-1-yl)carbonyl]cyclohexyl}benzene-sulfonamide,
N-{cis-4-[(4-isopropylpiperazin-1-yl)carbonyl]cyclohexyl}propane-2-sulfonamide,
N-{cis-4-[(4-isopropylpiperazin-1-yl)carbonyl]cyclohexyl}-2,4,6-trimethylbenzene-sulfonamide,
3-chloro-4-fluoro-N-{cis-4-[(4-isopropylpiperazin-1-yl)carbonyl]cyclohexyl}benzene-sulfonamide,
2,4-dichloro-N-{cis-4-[(4-isopropylpiperazin-1-yl)carbonyl]cyclohexyl}benzene-sulfonamide,
3,4-dichloro-N-{cis-4-[(4-isopropylpiperazin-1-yl)carbonyl]cyclohexyl}benzene-sulfonamide,
3,4,5-trifluoro-N-{cis-4-[(4-isopropylpiperazin-1-yl)carbonyl]cyclohexyl}benzene-sulfonamide,
5-fluoro-N-{cis-4-[(4-isopropylpiperazin-1-yl)carbonyl]cyclohexyl}-2-methylbenzene-sulfonamide,
4-chloro-2-fluoro-N-{cis-4-[(4-isopropylpiperazin-1-yl)carbonyl]cyclohexyl}benzene-sulfonamide,
2-chloro-N-{cis-4-[(4-isopropylpiperazin-1-yl)carbonyl]cyclohexyl}benzenesulfonamide,
3,4-difluoro-N-{cis-4-[(4-isopropylpiperazin-1-yl)carbonyl]cyclohexyl}benzene-sulfonamide,
N-{cis-4-[(4-isopropylpiperazin-1-yl)carbonyl]cyclohexyl}-1-[3-(trifluoromethyl)-phenyl]methanesulfonamide,
N-{cis-4-[(4-isopropylpiperazin-1-yl)carbonyl]cyclohexyl}-1-[4-(trifluoromethyl)-phenyl]methanesulfonamide,
1-(3,4-dichlorophenyl)-N-{cis-4-[(4-isopropylpiperazin-1-yl)carbonyl]cyclohexyl}-methanesulfonamide,
2-cyano-N-{trans-4-[(4-isopropylpiperazin-1-yl)carbonyl]cyclohexyl}benzene-sulfonamide,
N-{trans-4-[(4-isopropylpiperazin-1-yl)carbonyl]cyclohexyl}-4-(trifluoromethoxy)-benzenesulfonamide,
3,4,5-trifluoro-N-{trans-4-[(4-isopropylpiperazin-1-yl)carbonyl]cyclohexyl}benzene-sulfonamide,
5-fluoro-N-{trans-4-[(4-isopropylpiperazin-1-yl)carbonyl]cyclohexyl}-2-methylbenzene-sulfonamide,
4-chloro-2-fluoro-N-{trans-4-[(4-isopropylpiperazin-1-yl)carbonyl]cyclohexyl}benzene-sulfonamide,
4-chloro-N-{trans-4-[(4-isopropylpiperazin-1-yl)carbonyl]cyclohexyl}benzene-sulfonamide,
2-chloro-N-{trans-4-[(4-isopropylpiperazin-1-yl)carbonyl]cyclohexyl}benzene-sulfonamide,
4-acetyl-N-{trans-4-[(4-isopropylpiperazin-1-yl)carbonyl]cyclohexyl}benzene-sulfonamide,
3,4-difluoro-N-{trans-4-[(4-isopropylpiperazin-1-yl)carbonyl]cyclohexyl}benzene-sulfonamide,
N-{trans-4-[(4-isopropylpiperazin-1-yl)carbonyl]cyclohexyl}-1-[3-(trifluoromethyl)-phenyl]methanesulfonamide,
N-{trans-4-[(4-isopropylpiperazin-1-yl)carbonyl]cyclohexyl}-1-[4-(trifluoromethyl)-phenyl]methanesulfonamide,
1-(3,4-dichlorophenyl)-N-{trans-4-[(4-isopropylpiperazin-1-yl)carbonyl]cyclohexyl}-methanesulfonamide,
3-cyano-4-fluoro-N-[trans-4-(4-isopropyl-piperazine-1-carbonyl)-cyclohexyl]-benzenesulfonamide,
N-{trans-4-[4-(4-isopropyl-piperazine-1-carbonyl)-cyclohexylsulfamoyl]-phenyl}-acetamide,
N-[trans-4-(4-isopropyl-piperazine-1-carbonyl)-cyclohexyl]-4-methanesulfonyl-benzenesulfonamide,
6-chloro-pyridine-3-sulfonic acid[trans-4-(4-isopropyl-piperazine-1-carbonyl)-cyclohexyl]-amide,
N-[trans-4-(4-isopropyl-piperazine-1-carbonyl)-cyclohexyl]-2,N-dimethyl-benzenesulfonamide,
2,4-difluoro-N-[trans-4-(4-isopropyl-piperazine-1-carbonyl)-cyclohexyl]-N-methyl-benzenesulfonamide,
N-[trans-4-(4-isopropyl-piperazine-1-carbonyl)-cyclohexyl]-2,4,6,N-tetramethyl-benzenesulfonamide,
3-chloro-4-fluoro-N-[trans-4-(4-isopropyl-piperazine-1-carbonyl)-cyclohexyl]-N-methyl-benzenesulfonamide,
N-[trans-4-(4-isopropyl-piperazine-1-carbonyl)-cyclohexyl]-N-methyl-4-trifluoromethyl-benzenesulfonamide,
3,4-dichloro-N-[trans-4-(4-isopropyl-piperazine-1-carbonyl)-cyclohexyl]-N-methyl-benzenesulfonamide,
2-cyano-N-[trans-4-(4-isopropyl-piperazine-1-carbonyl)-cyclohexyl]-N-methyl-benzenesulfonamide,
N-[trans-4-(4-isopropyl-piperazine-1-carbonyl)-cyclohexyl]-N-methyl-4-trifluoromethoxy-benzenesulfonamide,
4-cyano-N-[trans-4-(4-isopropyl-piperazine-1-carbonyl)-cyclohexyl]-N-methyl-benzenesulfonamide,
3-cyano-4-fluoro-N-[trans-4-(4-isopropyl-piperazine-1-carbonyl)-cyclohexyl]-N-methyl-benzenesulfonamide,
N-isopropyl-N-[trans-4-(4-isopropyl-piperazine-1-carbonyl)-cyclohexyl]-2-methyl-benzenesulfonamide,
N-isopropyl-N-[trans-4-(4-isopropyl-piperazine-1-carbonyl)-cyclohexyl]-4-methoxy-benzenesulfonamide,
2,4-difluoro-N-isopropyl-N-[trans-4-(4-isopropyl-piperazine-1-carbonyl)-cyclohexyl]-benzenesulfonamide,
N-isopropyl-N-[trans-4-(4-isopropyl-piperazine-1-carbonyl)-cyclohexyl]-2,4,6-trimethyl-benzenesulfonamide,
3-chloro-4-fluoro-N-isopropyl-N-[trans-4-(4-isopropyl-piperazine-1-carbonyl)-cyclohexyl]-benzenesulfonamide,
N-isopropyl-N-[trans-4-(4-isopropyl-piperazine-1-carbonyl)-cyclohexyl]-4-trifluoromethyl-benzenesulfonamide,
2-cyano-N-isopropyl-N-[trans-4-(4-isopropyl-piperazine-1-carbonyl)-cyclohexyl]-benzenesulfonamide,
N-isopropyl-N-[trans-4-(4-isopropyl-piperazine-1-carbonyl)-cyclohexyl]-4-trifluoromethoxy-benzenesulfonamide,
3-cyano-4-fluoro-N-isopropyl-N-[trans-4-(4-isopropyl-piperazine-1-carbonyl)-cyclohexyl]-benzenesulfonamide,
N-(4-{isopropyl-[trans-4-(4-isopropyl-piperazine-1-carbonyl)-cyclohexyl]-sulfamoyl}-phenyl)-acetamide,
6-chloro-pyridine-3-sulfonic acid isopropyl-[trans-4-(4-isopropyl-piperazine-1-carbonyl)-cyclohexyl]-amide,
N-cyclopropylmethyl-N-[trans-4-(4-isopropyl-piperazine-1-carbonyl)-cyclohexyl]-2-methyl-benzenesulfonamide,
N-cyclopropylmethyl-N-[trans-4-(4-isopropyl-piperazine-1-carbonyl)-cyclohexyl]-4-methoxy-benzenesulfonamide,
N-cyclopropylmethyl-2,4-difluoro-N-[trans-4-(4-isopropyl-piperazine-1-carbonyl)-cyclohexyl]-benzenesulfonamide, N-cyclopropylmethyl-N-[trans-4-(4-isopropyl-piperazine-1-carbonyl)-cyclohexyl]-2,4,6-trimethyl-benzenesulfonamide,
3-chloro-N-cyclopropylmethyl-4-fluoro-N-[trans-4-(4-isopropyl-piperazine-1-carbonyl)-cyclohexyl]-benzenesulfonamide,
N-cyclopropylmethyl-N-[trans-4-(4-isopropyl-piperazine-1-carbonyl)-cyclohexyl]-4-trifluoromethyl-benzenesulfonamide,
3,4-dichloro-N-cyclopropylmethyl-N-[trans-4-(4-isopropyl-piperazine-1-carbonyl)-cyclohexyl]-benzenesulfonamide,
2-cyano-N-cyclopropylmethyl-N-[trans-4-(4-isopropyl-piperazine-1-carbonyl)-cyclohexyl]-benzenesulfonamide,
N-cyclopropylmethyl-N-[trans-4-(4-isopropyl-piperazine-1-carbonyl)-cyclohexyl]-4-trifluoromethoxy-benzenesulfonamide,
4-acetyl-N-cyclopropylmethyl-N-[trans-4-(4-isopropyl-piperazine-1-carbonyl)-cyclohexyl]-benzenesulfonamide,
4-cyano-N-cyclopropylmethyl-N-[trans-4-(4-isopropyl-piperazine-1-carbonyl)-cyclohexyl]-benzenesulfonamide
3-cyano-N-cyclopropylmethyl-4-fluoro-N-[trans-4-(4-isopropyl-piperazine-1-carbonyl)-cyclohexyl]-benzenesulfonamide,
N-cyclopropylmethyl-N-[trans-4-(4-isopropyl-piperazine-1-carbonyl)-cyclohexyl]-4-methanesulfonyl-benzenesulfonamide,
6-chloro-pyridine-3-sulfonic acid cyclopropylmethyl-[trans-4-(4-isopropyl-piperazine-1-carbonyl)-cyclohexyl]-amide,
trans-N-[4-(4-cyclopentyl-piperazine-1-carbonyl)-cyclohexyl]-2-methyl-benzenesulfonamide,
trans-N-[4-(4-cyclopentyl-piperazine-1-carbonyl)-cyclohexyl]-2,4-difluoro-benzenesulfonamide,
trans-3-chloro-N-[4-(4-cyclopentyl-piperazine-1-carbonyl)-cyclohexyl]-4-fluoro-benzenesulfonamide,
trans-N-[4-(4-cyclopentyl-piperazine-1-carbonyl)-cyclohexyl]-4-trifluoro-methyl-benzenesulfonamide,
trans-N-[4-(4-cyclopentyl-piperazine-1-carbonyl)-cyclohexyl]-4-trifluoromethoxy-benzenesulfonamide,
trans-4-acetyl-N-[4-(4-cyclopentyl-piperazine-1-carbonyl)-cyclohexyl]-benzenesulfonamide,
trans-4-cyano-N-[4-(4-cyclopentyl-piperazine-1-carbonyl)-cyclohexyl]-benzenesulfonamide,
trans-3-cyano-N-[4-(4-cyclopentyl-piperazine-1-carbonyl)-cyclohexyl]-4-fluoro-benzenesulfonamide,
trans-N-[4-(4-cyclopentyl-piperazine-1-carbonyl)-cyclohexyl]-4-methanesulfonyl-benzenesulfonamide,
trans-6-chloro-pyridine-3-sulfonic acid [4-(4-cyclopentyl-piperazine-1-carbonyl)-cyclohexyl]-amide,
trans-N-[4-(4-cyclobutyl-piperazine-1-carbonyl)-cyclohexyl]-2-methyl-benzenesulfonamide,
trans-N-[4-(4-cyclobutyl-piperazine-1-carbonyl)-cyclohexyl]-2,4-difluoro-benzenesulfonamide,
trans-3-chloro-N-[4-(4-cyclobutyl-piperazine-1-carbonyl)-cyclohexyl]-4-fluoro-benzenesulfonamide,
trans-N-[4-(4-cyclobutyl-piperazine-1-carbonyl)-cyclohexyl]-4-trifluoromethyl-benzenesulfonamide,
trans-2-cyano-N-[4-(4-cyclobutyl-piperazine-1-carbonyl)-cyclohexyl]-benzenesulfonamide,
trans-N-[4-(4-cyclobutyl-piperazine-1-carbonyl)-cyclohexyl]-4-trifluoromethoxy-benzenesulfonamide,
trans-4-acetyl-N-[4-(4-cyclobutyl-piperazine-1-carbonyl)-cyclohexyl]-benzenesulfonamide,
trans-4-cyano-N-[4-(4-cyclobutyl-piperazine-1-carbonyl)-cyclohexyl]-benzenesulfonamide,
trans-3-cyano-N-[4-(4-cyclobutyl-piperazine-1-carbonyl)-cyclohexyl]-4-fluoro-benzenesulfonamide,
trans-N-{4-[4-(4-cyclo-butyl-piperazine-1-carbonyl)-cyclohexyl-sulfamoyl]-phenyl}-acetamide,
trans-N-[4-(4-cyclobutyl-piperazine-1-carbonyl)-cyclohexyl]-4-methane-sulfonyl-benzenesulfonamide,
trans-6-chloro-pyridine-3-sulfonic acid [4-(4-cyclobutyl-piperazine-1-carbonyl)-cyclohexyl]-amide,
trans-N-[4-(4-tert-butyl-piperazine-1-carbonyl)-cyclohexyl]-2-methyl-benzenesulfonamide,
trans-N-[4-(4-tert-butyl-piperazine-1-carbonyl)-cyclohexyl]-3-chloro-4-fluoro-benzenesulfonamide,
trans-N-[4-(4-tert-butyl-piperazine-1-carbonyl)-cyclohexyl]-4-trifluoromethoxy-benzenesulfonamide,
trans-N-[4-(4-tert-butyl-piperazine-1-carbonyl)-cyclohexyl]-4-cyano-benzenesulfonamide,
trans-thiophene-2-sulfonic acid[4-(4-isopropyl-piperazine-1-carbonyl)-cyclohexyl]-amide,
trans-3,5-dimethyl-isoxazole-4-sulfonic acid[4-(4-isopropyl-piperazine-1-carbonyl)-cyclohexyl]-amide,
trans-2,4-dimethyl-thiazole-5-sulfonic acid[4-(4-isopropyl-piperazine-1-carbonyl)-cyclohexyl]-amide,
trans-5-chloro-thiophene-2-sulfonic acid[4-(4-isopropyl-piperazine-1-carbonyl)-cyclohexyl]-amide,
trans-5-chloro-1,3-dimethyl-1H-pyrazole-4-sulfonic acid [4-(4-isopropyl-piperazine-1-carbonyl)-cyclohexyl]-amide,
trans-5-bromo-6-chloro-pyridine-3-sulfonic acid[4-(4-isopropyl-piperazine-1-carbonyl)-cyclohexyl]-amide,
trans-3-bromo-5-chloro-thiophene-2-sulfonic acid[4-(4-isopropyl-piperazine-1-carbonyl)-cyclohexyl]-amide,
trans-4-bromo-5-chloro-thiophene-2-sulfonic acid[4-(4-isopropyl-piperazine-1-carbonyl)-cyclohexyl]-amide,
trans-5-bromo-pyridine-3-sulfonic acid[4-(4-isopropyl-piperazine-1-carbonyl)-cyclohexyl]-amide,
trans-thiophene-2-sulfonic acid[4-(4-cyclopentyl-piperazine-1-carbonyl)-cyclohexyl]-amide,
trans-3,5-dimethyl-isoxazole-4-sulfonic acid[4-(4-cyclopentyl-piperazine-1-carbonyl)-cyclohexyl]-amide,
trans-5-chloro-thiophene-2-sulfonic acid[4-(4-cyclopentyl-piperazine-1-carbonyl)-cyclohexyl]-amide,
trans-5-chloro-1,3-dimethyl-1H-pyrazole-4-sulfonic acid[4-(4-cyclopentyl-piperazine-1-carbonyl)-cyclohexyl]-amide,
trans-4-bromo-5-chloro-thiophene-2-sulfonic acid[4-(4-cyclopentyl-piperazine-1-carbonyl)-cyclohexyl]-amide,
trans-thiophene-2-sulfonic acid[4-(4-cyclobutyl-piperazine-1-carbonyl)-cyclohexyl]-amide,
trans-2,3-dimethyl-3H-imidazole-4-sulfonic acid[4-(4-cyclobutyl-piperazine-1-carbonyl)-cyclohexyl]-amide,
trans-3,5-dimethyl-isoxazole-4-sulfonic acid[4-(4-cyclobutyl-piperazine-1-carbonyl)-cyclohexyl]-amide,
trans-2,4-dimethyl-thiazole-5-sulfonic acid[4-(4-cyclobutyl-piperazine-1-carbonyl)-cyclohexyl]-amide,
trans-5-chloro-thiophene-2-sulfonic acid[4-(4-cyclobutyl-piperazine-1-carbonyl)-cyclohexyl]-amide,
trans-5-chloro-1,3-dimethyl-1H-pyrazole-4-sulfonic acid[4-(4-cyclobutyl-piperazine-1-carbonyl)-cyclohexyl]-amide,
trans-5-bromo-6-chloro-pyridine-3-sulfonic acid[4-(4-cyclobutyl-piperazine-1-carbonyl)-cyclohexyl]-amide,
trans-3-bromo-5-chloro-thiophene-2-sulfonic acid[4-(4-cyclobutyl-piperazine-1-carbonyl)-cyclohexyl]-amide,
trans-4-bromo-5-chloro-thiophene-2-sulfonic acid[4-(4-cyclobutyl-piperazine-1-carbonyl)-cyclohexyl]-amide,
trans-thiophene-2-sulfonic acid[4-(4-tent-butyl-piperazine-1-carbonyl)-cyclohexyl]-amide,
trans-3,5-dimethyl-isoxazole-4-sulfonic acid[4-(4-tert-butyl-piperazine-1-carbonyl)-cyclohexyl]-amide,
trans-5-chloro-thiophene-2-sulfonic acid[4-(4-tert-butyl-piperazine-1-carbonyl)-cyclohexyl]-amide, trans-3-bromo-5-chloro-thiophene-2-sulfonic acid[4-(4-tert-butyl-piperazine-1-carbonyl)-cyclohexyl]-amide, trans-N-[4-(4-isopropyl-piperazine-1-carbonyl)-cyclohexyl]-2-methyl-N-(2,2,2-trifluoro-ethyl)-benzenesulfonamide, trans-N-[4-(4-isopropyl-piperazine-1-carbonyl)-cyclohexyl]-4-methoxy-N-(2,2,2-trifluoro-ethyl)-benzenesulfonamide, trans-2,4-difluoro-N-[4-(4-isopropyl-piperazine-1-carbonyl)-cyclohexyl]-N-(2,2,2-trifluoro-ethyl)-benzenesulfonamide, trans-N-[4-(4-isopropyl-piperazine-1-carbonyl)-cyclohexyl]-2,4,6-trimethyl-N-(2,2,2-trifluoro-ethyl)-benzenesulfonamide, trans-3-chloro-4-fluoro-N-[4-(4-isopropyl-piperazine-1-carbonyl)-cyclohexyl]-N-(2,2,2-trifluoro-ethyl)-benzenesulfonamide, trans-N-[4-(4-isopropyl-piperazine-1-carbonyl)-cyclohexyl]-N-(2,2,2-trifluoro-ethyl)-4-trifluoromethyl-benzenesulfonamide, trans-3,4-dichloro-N-[4-(4-isopropyl-piperazine-1-carbonyl)-cyclohexyl]-N-(2,2,2-trifluoro-ethyl)-benzenesulfonamide, trans-2-cyano-N-[4-(4-isopropyl-piperazine-1-carbonyl)-cyclohexyl]-N-(2,2,2-trifluoro-ethyl)-benzenesulfonamide, trans-N-[4-(4-isopropyl-piperazine-1-carbonyl)-cyclohexyl]-N-(2,2,2-trifluoro-ethyl)-4-trifluoromethoxy-benzenesulfonamide, trans-4-acetyl-N-[4-(4-isopropyl-piperazine-1-carbonyl)-cyclohexyl]-N-(2,2,2-trifluoro-ethyl)-benzenesulfonamide, trans-4-cyano-N-[4-(4-isopropyl-piperazine-1-carbonyl)-cyclohexyl]-N-(2,2,2-trifluoro-ethyl)-benzenesulfonamide, trans-3-cyano-4-fluoro-N-[4-(4-isopropyl-piperazine-1-carbonyl)-cyclohexyl]-N-(2,2,2-trifluoro-ethyl)-benzenesulfonamide, trans-N-{4-[[4-(4-isopropyl-piperazine-1-carbonyl)-cyclohexyl]-(2,2,2-trifluoro-ethyl)-sulfamoyl]-phenyl}-acetamide, trans-6-chloro-pyridine-3-sulfonic acid[4-(4-isopropyl-piperazine-1-carbonyl)-cyclohexyl]-(2,2,2-trifluoro-ethyl)-amide, trans)-N-[4-(4-isopropyl-piperazine-1-carbonyl)-cyclohexyl]-N-(2-methoxy-ethyl)-2-methyl-benzenesulfonamide, trans-2,4-difluoro-N-[4-(4-isopropyl-piperazine-1-carbonyl)-cyclohexyl]-N-(2-methoxy-ethyl)-benzenesulfonamide, trans-N-[4-(4-isopropyl-piperazine-1-carbonyl)-cyclohexyl]-N-(2-methoxy-ethyl)-2,4,6-trimethyl-benzenesulfonamide, trans-3-chloro-4-fluoro-N-[4-(4-isopropyl-piperazine-1-carbonyl)-cyclohexyl]-N-(2-methoxy-ethyl)-benzenesulfonamide, trans-N-[4-(4-Isopropyl-piperazine-1-carbonyl)-cyclohexyl]-N-(2-methoxy-ethyl)-4-trifluoromethyl-benzenesulfonamide, trans-3,4-dichloro-N-[4-(4-isopropyl-piperazine-1-carbonyl)-cyclohexyl]-N-(2-methoxy-ethyl)-benzenesulfonamide, trans-N-[4-(4-isopropyl-piperazine-1-carbonyl)-cyclohexyl]-N-(2-methoxy-ethyl)-4-trifluoromethoxy-benzenesulfonamide, trans-4-acetyl-N-[4-(4-isopropyl-piperazine-1-carbonyl)-cyclohexyl]-N-(2-methoxy-ethyl)-benzenesulfonamide, trans-4-cyano-N-[4-(4-isopropyl-piperazine-1-carbonyl)-cyclohexyl]-N-(2-methoxy-ethyl)-benzenesulfonamide, trans-N-{4-[[4-(4-Isopropyl-piperazine-1-carbonyl)-cyclohexyl]-(2-methoxy-ethyl)-sulfamoyl]-phenyl}-acetamide, trans-6-chloro-pyridine-3-sulfonic acid[4-(4-isopropyl-piperazine-1-carbonyl)-cyclohexyl]-(2-methoxy-ethyl)-amide, trans-4-cyano-N-[4-(4-cyclopropylmethyl-piperazine-1-carbonyl)-cyclohexyl]-benzenesulfonamide, trans-4-cyano-N-{4-[4-(tetrahydro-pyran-4-yl)-piperazine-1-carbonyl]-cyclohexyl}-benzenesulfonamide, and pharmaceutically acceptable salts thereof.

Especially preferred are the following compounds:

N-{trans-4-[(4-isopropylpiperazin-1-yl)carbonyl]cyclohexyl}-2-methylbenzene-sulfonamide, 4-cyano-N-{trans-4-[(4-isopropylpiperazin-1-yl)carbonyl]cyclohexyl}benzene-sulfonamide, 4-fluoro-N-{trans-4-[(4-isopropylpiperazin-1-yl)carbonyl]cyclohexyl}-2-methylbenzene-sulfonamide, 1-(3-fluorophenyl)-N-{trans-4-[(4-isopropylpiperazin-1-yl)carbonyl]cyclohexyl}-methanesulfonamide, N-{trans-4-[(4-isopropylpiperazin-1-yl)carbonyl]cyclohexyl}-2,4,6-trimethylbenzene-sulfonamide, 2,4-dichloro-N-{trans-4-[(4-isopropylpiperazin-1-yl)carbonyl]cyclohexyl}benzene-sulfonamide, 2-chloro-N-{trans-4-[(4-isopropylpiperazin-1-yl)carbonyl]cyclohexyl}benzene-sulfonamide, 3-chloro-4-fluoro-N-isopropyl-N-[trans-4-(4-isopropyl-piperazine-1-carbonyl)-cyclohexyl]-benzenesulfonamide, N-cyclopropylmethyl-N-[trans-4-(4-isopropyl-piperazine-1-carbonyl)-cyclohexyl]-2-methyl-benzenesulfonamide, N-cyclopropylmethyl-N-[trans-4-(4-isopropyl-piperazine-1-carbonyl)-cyclohexyl]-4-methoxy-benzenesulfonamide, N-cyclopropylmethyl-N-[trans-4-(4-isopropyl-piperazine-1-carbonyl)-cyclohexyl]-2,4,6-trimethyl-benzenesulfonamide, N-cyclopropylmethyl-N-[trans-4-(4-isopropyl-piperazine-1-carbonyl)-cyclohexyl]-4-trifluoromethoxy-benzenesulfonamide, trans-N-[4-(4-cyclopentyl-piperazine-1-carbonyl)-cyclohexyl]-2-methyl-benzenesulfonamide, trans-4-cyano-N-[4-(4-cyclopentyl-piperazine-1-carbonyl)-cyclohexyl]-benzenesulfonamide, trans-4-cyano-N-[4-(4-cyclobutyl-piperazine-1-carbonyl)-cyclohexyl]-benzenesulfonamide, trans-3-bromo-5-chloro-thiophene-2-sulfonic acid[4-(4-isopropyl-piperazine-1-carbonyl)-cyclohexyl]-amide, trans-3-bromo-5-chloro-thiophene-2-sulfonic acid[4-(4-cyclobutyl-piperazine-1-carbonyl)-cyclohexyl]-amide, trans-N-[4-(4-isopropyl-piperazine-1-carbonyl)-cyclohexyl]-2,4,6-trimethyl-N-(2,2,2-trifluoro-ethyl)-benzenesulfonamide, trans-N-[4-(4-isopropyl-piperazine-1-carbonyl)-cyclohexyl]-N-(2-methoxy-ethyl)-2,4,6-trimethyl-benzenesulfonamide, and pharmaceutically acceptable salts thereof.

In a further embodiment, the present invention relates to compounds of the general formula

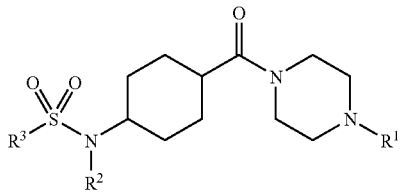

wherein
R¹ is lower alkyl or cycloalkyl;
R² is selected from the group consisting of hydrogen, lower alkyl, cycloalkyl, lower cycloalkylalkyl, lower halogenalkyl, lower alkoxyalkyl and lower cyanoalkyl;
R³ is selected from the group consisting of
lower alkyl,
—(CH$_2$)$_m$-aryl, wherein m is 0, 1 or 2 and wherein the aryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl,
—(CH$_2$)$_n$-heteroaryl, wherein n is 0, 1 or 2 and wherein the heteroaryl ring is unsubstituted or substituted with one or two groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl, and —NR⁴R⁵;
R⁴ is selected from the group consisting of hydrogen, lower alkyl, lower halogenalkyl, lower alkoxyalkyl and lower cyanoalkyl;
R⁵ is selected from the group consisting of lower alkyl, lower halogenalkyl, lower alkoxyalkyl, lower cyanoalkyl,
phenyl unsubstituted or substituted with one, two or three groups independently selected from lower alkyl, halogen, lower halogenalkyl, cyano, lower alkoxy, lower alkanoyl, benzoyl, lower halogenalkoxy and lower hydroxyalkyl, and
lower phenylalkyl wherein the phenyl ring may be unsubstituted or substituted with one or two groups independently selected from lower alkyl, halogen, lower halogenalkyl, cyano, lower alkoxy, lower alkanoyl, benzoyl, lower halogenalkoxy and lower hydroxyalkyl; or
R⁴ and R⁵ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group,
said heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen; and pharmaceutically acceptable salts thereof.
Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises
reacting a compound of formula II

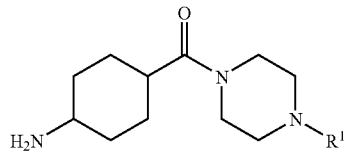

wherein R¹ is as defined herein before,
with an sulfonyl chloride of the formula III

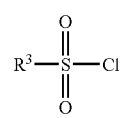

wherein R³ is as defined herein before, in the presence of a base to obtain a compound of the formula IA

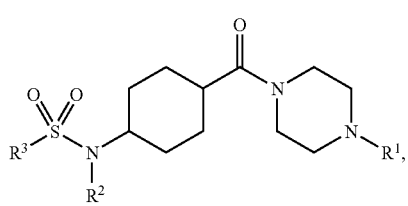

wherein R² is hydrogen, and optionally alkylating the compound of formula IA to obtain a compound of the formula IB

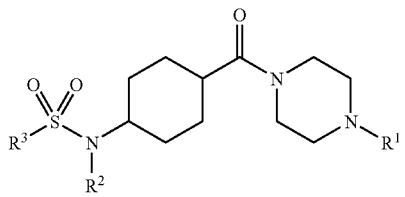

wherein R² is a group as defined herein before other than hydrogen, and if desired,
converting the compound obtained into a pharmaceutically acceptable acid addition salt.

"Alkylating" in this context means for example reacting the compound of formula IA with a suitable alcohol in the presence of a coupling reagent, preferably a phosphorane such as cyanomethylenetri-n-butylphosphorane.

The preparation of compounds of formula I of the present invention may be carried out in sequential or convergent synthetic routes. Syntheses of the invention are shown in the following scheme. The skills required for carrying out the reaction and purification of the resulting products are known to those skilled in the art. The substituents and indices used in the following description of the processes have the significance given herein before unless indicated to the contrary. In more detail, the compounds of formula I can be manufactured by the methods given below, by the methods given in the examples or by analogous methods. Appropriate reaction conditions for the individual reaction steps are known to a person skilled in the art.

Starting materials are either commercially available or can be prepared by methods analogous to the methods given below, by methods described in references cited in the description or in the examples, or by methods known in the art.

Compounds of formula I of the present invention can be prepared following the procedure as depicted in scheme 1.

4-tert-Butoxycarbonylamino-cyclohexanecarboxylic acid IV (cis or trans) is commercially available and can subsequently be modified at the acid functionality according to methods described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to transform the acid functionality in IV through amide coupling with substituted piperazines V (either commercially available or accessible by methods described in references or by methods known in the art; as appropriate) employing a coupling reagent. The reaction may be carried out in the presence or absence of a solvent and a base. There is no particular restriction on the nature of the solvent to be employed, provided that it has no adverse effect on the reaction or the reagents involved and that it can dissolve the reagents, at least to some extent. Examples for suitable solvents include: dimethylformamide (DMF), tetrahydrofuran (THF), dioxane, and the like. There is no particular restriction on the nature of the base used in this stage, and any base commonly used in this type of reaction may equally be employed here. Examples of such bases include NEt₃ or diisopropylethylamine (DIPEA), and the like. There is no particular restriction on the nature of the coupling reagent used in this stage, and any coupling reagent commonly used in this type of reaction may equally be employed here. Examples of such coupling reagents include N,N-carbonyldiimidazole (CDI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds VI.

Scheme 1

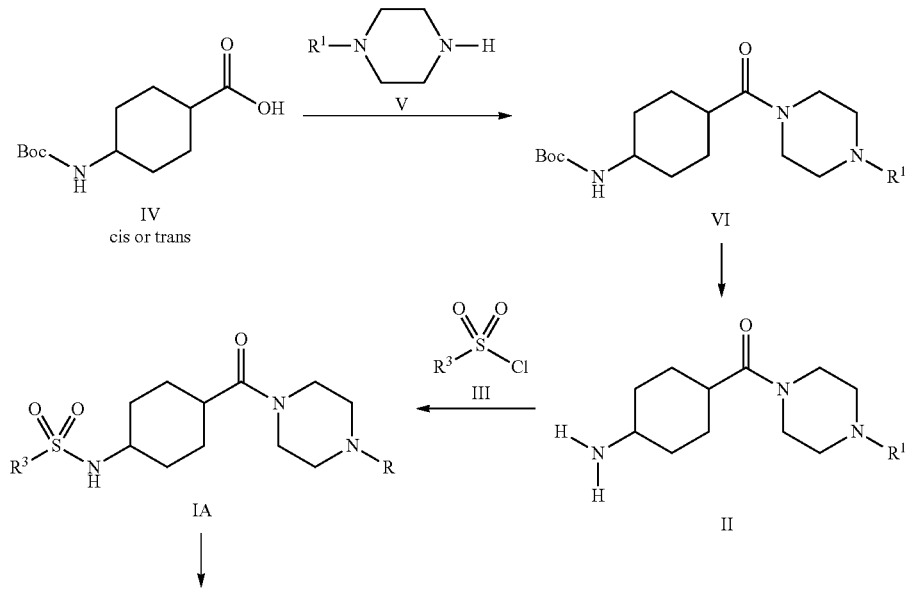

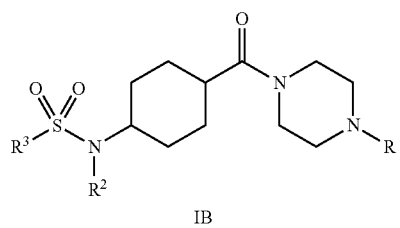

IB

Removal of the protecting group in VI can be affected under various conditions according to methods described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to cleave the Boc-protecting group under acidic conditions in the presence or the absence of a solvent to access the intermediate amine II. There is no particular restriction on the nature of the solvent to be employed, provided that it has no adverse effect on the reaction or the reagents involved and that it can dissolve the reagents, at least to some extent. Examples for suitable solvents include: dioxane, THF, water and the like. There is no particular restriction on the nature of the acid used in this stage, and any acid commonly used in this type of reaction may equally be employed here. Examples of such acids include HCl, acetic acid, and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the intermediate amine II.

The coupling of the intermediate amines II with sulfonyl chlorides III is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The respective amines can conveniently be transformed to the respective sulfonamides through coupling with a sulfonyl chloride (either commercially available or accessible by methods described in references or by methods known in the art; as appropriate). It is convenient to carry out the reaction in a solvent like dichloromethane (DCM) and in the presence of a base. There is no particular restriction on the nature of the solvent to be employed, provided that it has no adverse effect on the reaction or the reagents involved and that it can dissolve the reagents, at least to some extent. Examples for suitable solvents include: dichloromethane (DCM), dioxane, THF, and the like. There is no particular restriction on the nature of the base used in this stage, and any base commonly used in this type of reaction may equally be employed here. Examples of such bases include triethylamine and diisopropylethylamine (DIPEA), and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield sulfonamide derivatives IA ($R_2$=H).

The resulting compound of formula IA ($R_2$=H) is a compound of the present invention and may be the desired product. Alternatively, it may be subjected to consecutive reactions like alkylation of the sulphonamide under suitable conditions. There are various reaction conditions known in literature to affect such transformations. However, it is convenient to convert sulfonamides IA ($R_2$=H) to sulfonamides IB ($R_2$=a group selected from lower alkyl, cycloalkyl, lower cycloalkylalkyl, lower halogenalkyl, lower alkoxyalkyl and lower cyanoalkyl) by reaction of IA ($R_2$=H) with suitable alcohols in the presence of a coupling reagent like a phosphorane (adapted from: THL 2002, 43, 2187-2190). The reaction can be carried out in the presence or absence of a solvent. There is no particular restriction on the nature of the solvent to be employed, provided that it has no adverse effect on the reaction or the reagents involved and that it can dissolve the reagents, at least to some extent. Examples for suitable solvents include toluene and the like. There is no particular restriction on the nature of the phosphorane used in this stage provided it affects the reaction. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield sulfonamides IB ($R_2$=a group selected from lower alkyl, cycloalkyl, lower cycloalkylalkyl, lower halogenalkyl, lower alkoxyalkyl and lower cyanoalkyl).

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred embodiment of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) -Glucosidase inhibitors such as acarbose (precose) or miglitol (glyset), and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165, and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).
Binding Assay with $^3$H-(R)α-methylhistamine Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 µl final volume in 96-well plates in presence of $^3H(R)\alpha$-Methylhistamine (1 nM final concentration=Kd). Non-specific binding was determined using a 200 fold excess of cold $(R)\alpha$-Methylhistamine dihydrobromide.

All compounds were tested at a single concentration in duplicates. Compounds that showed an inhibition of $[^3H]$-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 1 | 54.8 |
| Example 15 | 23.4 |
| Example 64 | 8.9 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragés, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Example 1

N-{trans-4-[(4-isopropylpiperazin-1-yl)carbonyl]cyclohexyl}propane-1-sulfonamide

Step 1: [trans-4-(4-Isopropyl-piperazine-1-carbonyl)-cyclohexyl]-carbamic acid tert-butyl ester

A mixture of 3 g (12 mmol) 4-tert-butoxycarbonylamino-trans-cyclohexane carboxylic acid (commercially available), 1.74 g (14 mmol) 1-(2-propyl)-piperazine (commercially available), 4.75 g (15 mmol) TBTU and 3.64 g (36 mmol) NEt$_3$ in 10 ml DMF was stirred for 3 h at room temperature. After evaporation the residue was washed with 1N NaHCO$_3$ solution, extracted with DCM and the combined organic layers dried with MgSO$_4$ and evaporated to dryness to yield 4.56 g (94%) of the title compound. MS (m/e): 354.3 (MH$^+$).

Step 2: trans-(4-amino-cyclohexyl)-(4-isopropyl-piperazin-1-yl)-methanone, dihydrochloride (intermediate 1)

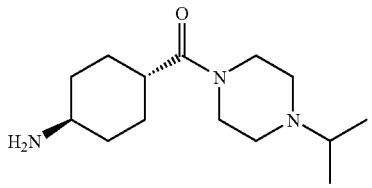

A mixture of 4.56 g (12 mmol) [trans-4-(4-isopropyl-piperazine-1-carbonyl)-cyclohexyl]-carbamic acid tert-butyl ester and 29 mL 4N HCl in dioxane was stirred for 6 h at 50° C. evaporated to dryness and used without further purification in the subsequent step. MS (m/e): 254.1 (MH$^+$).

Step 3: N-{trans-4-[(4-isopropylpiperazin-1-yl)carbonyl]cyclohexyl}propane-1-sulfonamide

A mixture of 32.6 mg (0.1 mmol) trans-(4-amino-cyclohexyl)-(4-isopropyl-piperazin-1-yl)-methanone, dihydrochloride, 28 mg (0.2 mmol) propane-1-sulfonyl chloride and 101 mg (1 mmol) NEt$_3$ in 2 ml DCM was stirred for 16 h at 40° C. After evaporation methanol and DMF were added and the mixture was subjected to preparative HPLC purification on reversed phase eluting with a gradient of acetonitrile/water (0.1% NEt$_3$). The combined product fractions were evaporated to dryness to yield 13.9 mg (39%) of the title compound. MS (m/e): 360.4 (MH$^+$).

Intermediate 2 cis-(4-Amino-cyclohexyl)-(4-isopropyl-piperazin-1-yl)-methanone, dihydrochloride

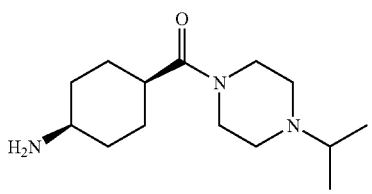

Step 1: [cis-4-(4-Isopropyl-piperazine-1-carbonyl)-cyclohexyl]-carbamic acid tert-butyl ester

According to the procedure described for the synthesis of [trans-4-(4-isopropyl-piperazine-1-carbonyl)-cyclohexyl]-carbamic acid tert-butyl ester the title compound was synthesized from 4-tert-butoxycarbonylamino-cis-cyclohexanecarboxylic acid (commercially available) and 1-(2-propyl)-piperazine (commercially available). MS (m/e): 354.3 (MH$^+$).

Step 2: cis-(4-Amino-cyclohexyl)-(4-isopropyl-piperazin-1-yl)-methanone, dihydrochloride

According to the procedure described for the synthesis of trans-(4-amino-cyclohexyl)-(4-isopropyl-piperazin-1-yl)-methanone, dihydrochloride the title compound was synthesized from [cis-4-(4-Isopropyl-piperazine-1-carbonyl)-cyclohexyl]-carbamic acid tert-butyl ester. MS (m/e): 254.4 (MH$^+$).

Intermediate 3 trans-(4-Amino-cyclohexyl)-(4-cyclopentyl-piperazin-1-yl)-methanone, dihydrochloride

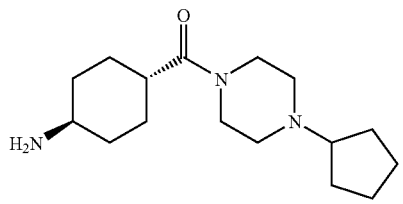

In analogy to the procedure described for the synthesis of trans-(4-amino-cyclohexyl)-(4-isopropyl-piperazin-1-yl)-methanone, dihydrochloride (intermediate 1) the title compound was prepared from 4-tert-butoxycarbonylamino-trans-cyclohexane carboxylic acid (commercially available) and cyclopentyl-piperazine (commercially available) followed by acidic cleavage of the tert-butylcarbonyloxy protecting group. MS (m/e): 280.1 (MH$^+$).

Intermediate 4 trans-(4-Amino-cyclohexyl)-(4-cyclobutyl-piperazin-1-yl)-methanone; dihydrochloride

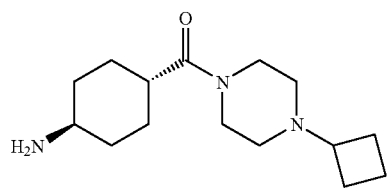

In analogy to the procedure described for the synthesis of trans-(4-amino-cyclohexyl)-(4-isopropyl-piperazin-1-yl)-methanone, dihydrochloride (intermediate 1) the title compound was prepared from 4-tert-butoxycarbonylamino-trans-cyclohexane carboxylic acid (commercially available) and 1-cyclobutyl-piperazine (commercially available) followed by acidic cleavage of the tert-butylcarbonyloxy protecting group. MS (m/e): 266.1 (MH+).

Intermediate 5 trans-(4-Amino-cyclohexyl)-(4-tert-butyl-piperazin-1-yl)-methanone, dihydrochloride

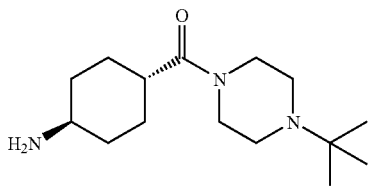

In analogy to the procedure described for the synthesis of trans-(4-amino-cyclohexyl)-(4-isopropyl-piperazin-1-yl)-methanone, dihydrochloride (intermediate 1) the title compound was prepared from 4-tert-butoxycarbonylamino-trans-cyclohexane carboxylic acid (commercially available) and 1-tert-butyl-piperazine (commercially available) followed by acidic cleavage of the tert-butylcarbonyloxy protecting group. MS (m/e): 268.1 (MH+).

According to the procedure described for example 1 further piperazinyl-carbonyl-cyclohexyl sulfonamide derivatives have been synthesized from their respective starting materials mentioned in table 1. Table 1 comprises example 2 to example 49.

TABLE 1

| Ex. No. | MW | Name | Starting materials | MW found (MH+) |
|---|---|---|---|---|
| 2 | 359.5 | N-{trans-4-[(4-isopropyl-piperazin-1-yl)carbonyl]cyclohexyl}propane-2-sulfonamide | trans-(4-amino-cyclohexyl)-(4-isopropyl-piperazin-1-yl)-methanone (intermediate 1) and propane-2-sulfonyl chloride (commercially available) | 360.4 |
| 3 | 360.5 | N'-{trans-4-[(4-isopropyl-piperazin-1-yl)carbonyl]cyclohexyl}-N,N-dimethylsulfamide | trans-(4-amino-cyclohexyl)-(4-isopropyl-piperazin-1-yl)-methanone (intermediate 1) and N,N-dimethylamino-sulfamoylchloride (commercially available) | 361.4 |
| 4 | 407.6 | N-{trans-4-[(4-isopropylpiperazin-1-yl)carbonyl]cyclohexyl}-2-methylbenzenesulfonamide | trans-(4-amino-cyclohexyl)-(4-isopropyl-piperazin-1-yl)-methanone (intermediate 1) and 2-methyl-benzenesulfonyl chloride (commercially available) | 408.4 |
| 5 | 411.5 | 2-fluoro-N-{trans-4-[(4-isopropylpiperazin-1-yl)carbonyl]cyclohexyl}benzenesulfonamide | trans-(4-amino-cyclohexyl)-(4-isopropyl-piperazin-1-yl)-methanone (intermediate 1) and 2-fluoro-benzenesulfonyl chloride (commercially available) | 412.4 |
| 6 | 411.5 | 4-fluoro-N-{trans-4-[(4-isopropylpiperazin-1-yl)carbonyl]cyclohexyl}benzenesulfonamide | trans-(4-amino-cyclohexyl)-(4-isopropyl-piperazin-1-yl)-methanone (intermediate 1) and 4-fluoro-benzenesulfonyl chloride (commercially available) | 412.4 |
| 7 | 418.6 | 4-cyano-N-{trans-4-[(4-isopropylpiperazin-1-yl)carbonyl]cyclohexyl}-benzenesulfonamide | trans-(4-amino-cyclohexyl)-(4-isopropyl-piperazin-1-yl)-methanone (intermediate 1) and 4-cyano-benzenesulfonyl chloride (commercially available) | 419.3 |
| 8 | 423.6 | N-{trans-4-[(4-isopropyl-piperazin-1-yl)carbonyl]cyclohexyl}-4-methoxy-benzenesulfonamide | trans-(4-amino-cyclohexyl)-(4-isopropyl-piperazin-1-yl)-methanone (intermediate 1) and 4-methoxy-benzenesulfonyl chloride (commercially available) | 424.3 |
| 9 | 423.6 | N-{trans-4-[(4-isopropyl-piperazin-1-yl)carbonyl]cyclohexyl}-3-methoxy-benzenesulfonamide | trans-(4-amino-cyclohexyl)-(4-isopropyl-piperazin-1-yl)-methanone (intermediate 1) and 3-methoxy-benzenesulfonyl chloride (commercially available) | 424.3 |
| 10 | 425.6 | 4-fluoro-N-{trans-4-[(4-isopropylpiperazin-1-yl)carbonyl]cyclohexyl}-2-methylbenzenesulfonamide | trans-(4-amino-cyclohexyl)-(4-isopropyl-piperazin-1-yl)-methanone (intermediate 1) and 4-fluoro-2-methyl-benzenesulfonyl chloride (commercially available) | 426.3 |
| 11 | 425.6 | 1-(3-fluorophenyl)-N-{trans-4-[(4-isopropyl-piperazin-1-yl)carbonyl]-cyclohexyl}-methanesulfonamide | trans-(4-amino-cyclohexyl)-(4-isopropyl-piperazin-1-yl)-methanone (intermediate 1) and (3-fluoro-phenyl)-methanesulfonyl chloride (commercially available) | 426.3 |
| 12 | 429.5 | 2,4-difluoro-N-{trans-4-[(4-isopropylpiperazin-1-yl)carbonyl]cyclohexyl}-benzenesulfonamide | trans-(4-amino-cyclohexyl)-(4-isopropyl-piperazin-1-yl)-methanone (intermediate 1) and 2,4-difluoro-benzenesulfonyl chloride (commercially available) | 430.4 |
| 13 | 435.6 | N-{trans-4-[(4-isopropyl-piperazin-1-yl)carbonyl]-cyclohexyl}-2,4,6-trimethyl-benzenesulfonamide | trans-(4-amino-cyclohexyl)-(4-isopropyl-piperazin-1-yl)-methanone (intermediate 1) and 2,4,6-trimethyl-benzenesulfonyl chloride (commercially available) | 436.4 |
| 14 | 446 | 3-chloro-4-fluoro-N-{trans-4-[(4-isopropylpiperazin-1-yl)carbonyl]cyclohexyl}-benzenesulfonamide | trans-(4-amino-cyclohexyl)-(4-isopropyl-piperazin-1-yl)-methanone (intermediate 1) and 3-chloro-4-fluoro-benzenesulfonyl chloride (commercially available) | 446.3 |
| 15 | 453.6 | N-{trans-4-[(4-isopropyl-piperazin-1-yl)carbonyl]-cyclohexyl}-2,4-dimethoxy-benzenesulfonamide | trans-(4-amino-cyclohexyl)-(4-isopropyl-piperazin-1-yl)-methanone (intermediate 1) and 2,4-dimethoxy-benzenesulfonyl chloride (commercially available) | 454.3 |
| 16 | 453.6 | N-{trans-4-[(4-isopropyl-piperazin-1-yl)carbonyl]-cyclohexyl}-2,5-dimethoxy-benzenesulfonamide | trans-(4-amino-cyclohexyl)-(4-isopropyl-piperazin-1-yl)-methanone (intermediate 1) and 2,5-dimethoxybenzene-sulfonyl chloride (commercially available) | 454.3 |
| 17 | 453.6 | N-{trans-4-[(4-isopropyl-piperazin-1-yl)carbonyl]-cyclohexyl}-3,4-dimethoxy- | trans-(4-amino-cyclohexyl)-(4-isopropyl-piperazin-1-yl)-methanone (intermediate 1) and 3,4-dimethoxy- | 454.3 |

TABLE 1-continued

| Ex. No. | MW | Name | Starting materials | MW found (MH+) |
|---|---|---|---|---|
| 18 | 461.5 | N-{trans-4-[(4-isopropyl-piperazin-1-yl)carbonyl]-cyclohexyl}-4-(trifluoro-methyl)benzene-sulfonamide | benzenesulfonyl chloride (commercially available) trans-(4-amino-cyclohexyl)-(4-isopropyl-piperazin-1-yl)-methanone (intermediate 1) and 4-trifluoromethyl-benzenesulfonyl chloride (commercially available) | 462.4 |
| 19 | 462.4 | 2,4-dichloro-N-{trans-4-[(4-isopropylpiperazin-1-yl)carbonyl]cyclo-hexyl}-benzenesulfonamide | trans-(4-amino-cyclohexyl)-(4-isopropyl-piperazin-1-yl)-methanone (intermediate 1) and 2,4-dichlorobenzenesulfonyl chloride (commercially available) | 462.3 |
| 20 | 462.4 | 3,4-dichloro-N-{trans-4-[(4-isopropylpiperazin-1-yl)carbonyl]cyclo-hexyl}-benzenesulfonamide | trans-(4-amino-cyclohexyl)-(4-isopropyl-piperazin-1-yl)-methanone (intermediate 1) and 3,4-dichlorobenzenesulfonyl chloride (commercially available) | 462.3 |
| 21 | 359.5 | N-{cis-4-[(4-isopropyl-piperazin-1-yl)carbonyl]-cyclohexyl}-propane-2-sulfonamide | cis-(4-amino-cyclohexyl)-(4-isopropyl-piperazin-1-yl)-methanone (intermediate 2) and propane-2-sulfonyl chloride (commercially available) | 360.4 |
| 22 | 435.6 | N-{cis-4-[(4-isopropyl-piperazin-1-yl)carbonyl]-cyclohexyl}-2,4,6-trimethyl-benzenesulfonamide | cis-(4-amino-cyclohexyl)-(4-isopropyl-piperazin-1-yl)-methanone (intermediate 2) and 2,4,6-trimethyl-benzenesulfonyl chloride (commercially available) | 436.4 |
| 23 | 446 | 3-chloro-4-fluoro-N-{cis-4-[(4-isopropylpiperazin-1-yl)carbonyl]cyclo-hexyl}-benzenesulfonamide | cis-(4-amino-cyclohexyl)-(4-isopropyl-piperazin-1-yl)-methanone (intermediate 2) and 3-chloro-4-fluoro-benzenesulfonyl chloride (commercially available) | 446.2 |
| 24 | 462.4 | 2,4-dichloro-N-{cis-4-[(4-isopropylpiperazin-1-yl)carbonyl]cyclo-hexyl}benzene-sulfonamide | cis-(4-amino-cyclohexyl)-(4-isopropyl-piperazin-1-yl)-methanone (intermediate 2) and 2,4-dichlorobenzenesulfonyl chloride (commercially available) | 462.3 |
| 25 | 462.4 | 3,4-dichloro-N-{cis-4-[(4-isopropylpiperazin-1-yl)carbonyl]cyclo-hexyl}-benzenesulfonamide | cis-(4-amino-cyclohexyl)-(4-isopropyl-piperazin-1-yl)-methanone (intermediate 2) and 3,4-dichlorobenzenesulfonyl chloride (commercially available) | 462.3 |
| 26 | 447.5 | 3,4,5-trifluoro-N-{cis-4-[(4-isopropylpiperazin-1-yl)carbonyl]cyclo-hexyl}-benzenesulfonamide | cis-(4-amino-cyclohexyl)-(4-isopropyl-piperazin-1-yl)-methanone (intermediate 2) and 3,4,5-trifluorobenzenesulfonyl chloride (commercially available) | 448.2 |
| 27 | 425.6 | 5-fluoro-N-{cis-4-[(4-isopropylpiperazin-1-yl)carbonyl]cyclo-hexyl}-2-methylbenzene-sulfonamide | cis-(4-amino-cyclohexyl)-(4-isopropyl-piperazin-1-yl)-methanone (intermediate 2) and 5-fluoro-2-methyl-benzenesulfonyl chloride (commercially available) | 426.3 |
| 28 | 446 | 4-chloro-2-fluoro-N-{cis-4-[(4-isopropylpiperazin-1-yl)carbonyl]cyclo-hexyl}benzene-sulfonamide | cis-(4-amino-cyclohexyl)-(4-isopropyl-piperazin-1-yl)-methanone (intermediate 2) and 4-chloro-2-fluoro-benzenesulfonyl chloride (commercially available) | 446.3 |
| 29 | 428 | 2-chloro-N-{cis-4-[(4-isopropylpiperazin-1-yl)carbonyl]cyclo-hexyl}-benzenesulfonamide | cis-(4-amino-cyclohexyl)-(4-isopropyl-piperazin-1-yl)-methanone (intermediate 2) and 2-chloro-benzenesulfonyl chloride (commercially available) | 428.3 |
| 30 | 429.5 | 3,4-difluoro-N-{cis-4-[(4-isopropylpiperazin-1-yl)carbonyl]cyclo-hexyl}-benzenesulfonamide | cis-(4-amino-cyclohexyl)-(4-isopropyl-piperazin-1-yl)-methanone (intermediate 2) and 3,4-difluoro-benzenesulfonyl chloride (commercially available) | 430.4 |
| 31 | 475.6 | N-{cis-4-[(4-isopropyl-piperazin-1-yl)carbonyl]-cyclohexyl}-1-[3-(trifluoro-methyl)phenyl]-methanesulfonamide | cis-(4-amino-cyclohexyl)-(4-isopropyl-piperazin-1-yl)-methanone (intermediate 2) and (3-trifluoromethyl-phenyl)-methanesulfonyl chloride (commercially available) | 476.3 |
| 32 | 475.6 | N-{cis-4-[(4-isopropyl-piperazin-1-yl)carbonyl]-cyclohexyl}-1-[4-(trifluoro-methyl)phenyl]-methanesulfonamide | cis-(4-amino-cyclohexyl)-(4-isopropyl-piperazin-1-yl)-methanone (intermediate 2) and (4-trifluoromethyl-phenyl)-methanesulfonyl chloride (commercially available) | 476.3 |
| 33 | 476.5 | 1-(3,4-dichlorophenyl)-N-{cis-4-[(4-isopropyl-piperazin-1-yl)carbonyl]-cyclohexyl}-methanesulfonamide | cis-(4-amino-cyclohexyl)-(4-isopropyl-piperazin-1-yl)-methanone (intermediate 2) and (3,4-dichloro-phenyl)-methanesulfonyl chloride (commercially available) | 476.2 |
| 34 | 418.6 | 2-cyano-N-{trans-4-[(4-isopropylpiperazin-1-yl)carbonyl]cyclo-hexyl}-benzenesulfonamide | trans-(4-amino-cyclohexyl)-(4-isopropyl-piperazin-1-yl)-methanone (intermediate 1) and 2-cyano-benzenesulfonyl chloride (commercially available) | 419.3 |
| 35 | 477.5 | N-{trans-4-[(4-isopropyl-piperazin-1-yl)carbonyl]-cyclohexyl}-4-(trifluoro-methoxy)benzene-sulfonamide | trans-(4-amino-cyclohexyl)-(4-isopropyl-piperazin-1-yl)-methanone (intermediate 1) and 4-trifluoromethoxy-benzenesulfonyl chloride (commercially available) | 478.2 |
| 36 | 447.5 | 3,4,5-trifluoro-N-{trans-4-[(4-isopropylpiperazin-1-yl)carbonyl]cyclo-hexyl}-benzenesulfonamide | trans-(4-amino-cyclohexyl)-(4-isopropyl-piperazin-1-yl)-methanone (intermediate 1) and 3,4,5-trifluoro-benzenesulfonyl chloride (commercially available) | 448.2 |
| 37 | 425.6 | 5-fluoro-N-{trans-4-[(4-isopropylpiperazin-1-yl)carbonyl]cyclo-hexyl}-2-methylbenzene-sulfonamide | trans-(4-amino-cyclohexyl)-(4-isopropyl-piperazin-1-yl)-methanone (intermediate 1) and 5-fluoro-2-methyl-benzenesulfonyl chloride (commercially available) | 426.3 |
| 38 | 446 | 4-chloro-2-fluoro-N-{trans-4-[(4-isopropylpiperazin-1-yl)carbonyl]cyclo-hexyl}-benzenesulfonamide | trans-(4-amino-cyclohexyl)-(4-isopropyl-piperazin-1-yl)-methanone (intermediate 1) and 4-chloro-2-fluoro-benzenesulfonyl chloride (commercially available) | 446.3 |
| 39 | 428 | 4-chloro-N-{trans-4-[(4- | trans-(4-amino-cyclohexyl)-(4-isopropyl-piperazin-1-yl)- | 428.3 |

TABLE 1-continued

| Ex. No. | MW | Name | Starting materials | MW found (MH+) |
|---|---|---|---|---|
| | | isopropylpiperazin-1-yl)carbonyl]cyclohexyl}-benzenesulfonamide | methanone (intermediate 1) and 4-chloro-benzenesulfonyl chloride (commercially available) | |
| 40 | 428 | 2-chloro-N-{trans-4-[(4-isopropylpiperazin-1-yl)carbonyl]cyclohexyl}-benzenesulfonamide | trans-(4-amino-cyclohexyl)-(4-isopropyl-piperazin-1-yl)-methanone (intermediate 1) and 2-chloro-benzenesulfonyl chloride (commercially available) | 428.3 |
| 41 | 435.6 | 4-acetyl-N-{trans-4-[(4-isopropylpiperazin-1-yl)carbonyl]cyclohexyl}-benzenesulfonamide | trans-(4-amino-cyclohexyl)-(4-isopropyl-piperazin-1-yl)-methanone (intermediate 1) and 4-acetyl-benzenesulfonyl chloride (commercially available) | 436.4 |
| 42 | 429.5 | 3,4-difluoro-N-{trans-4-[(4-isopropylpiperazin-1-yl)carbonyl]cyclohexyl}-benzenesulfonamide | trans-(4-amino-cyclohexyl)-(4-isopropyl-piperazin-1-yl)-methanone (intermediate 1) and 3,4-difluoro-benzenesulfonyl chloride (commercially available) | 430.4 |
| 43 | 475.6 | N-{trans-4-[(4-isopropyl-piperazin-1-yl)carbonyl]-cyclohexyl}-1-[3-(trifluoromethyl)phenyl]-methanesulfonamide | trans-(4-amino-cyclohexyl)-(4-isopropyl-piperazin-1-yl)-methanone (intermediate 1) and (3-trifluoromethyl-phenyl)-methanesulfonyl chloride (commercially available) | 476.3 |
| 44 | 475.6 | N-{trans-4-[(4-isopropyl-piperazin-1-yl)carbonyl]-cyclohexyl}-1-[4-(trifluoromethyl)phenyl]-methanesulfonamide | trans-(4-amino-cyclohexyl)-(4-isopropyl-piperazin-1-yl)-methanone (intermediate 1) and (4-trifluoromethyl-phenyl)-methanesulfonyl chloride (commercially available) | 476.3 |
| 45 | 476.5 | 1-(3,4-dichlorophenyl)-N-{trans-4-[(4-isopropyl-piperazin-1-yl)carbonyl]-cyclohexyl}-methanesulfonamide | trans-(4-amino-cyclohexyl)-(4-isopropyl-piperazin-1-yl)-methanone (intermediate 1) and (3,4-dichloro-phenyl)-methanesulfonyl chloride (commercially available) | 476.2 |
| 46 | 436.5 | 3-cyano-4-fluoro-N-[trans-4-(4-isopropyl-piperazine-1-carbonyl)-cyclohexyl]-benzenesulfonamide | trans-(4-amino-cyclohexyl)-(4-isopropyl-piperazin-1-yl)-methanone (intermediate 1) and 3-cyano-4-fluoro-benzenesulfonyl chloride (commercially available) | 437.1 |
| 47 | 450.6 | N-{trans-4-[4-(4-Isopropyl-piperazine-1-carbonyl)-cyclohexylsulfamoyl]-phenyl}-acetamide | trans-(4-amino-cyclohexyl)-(4-isopropyl-piperazin-1-yl)-methanone (intermediate 1) and 4-acetylamino-benzenesulfonyl chloride (commercially available) | 451.1 |
| 48 | 471.6 | N-[trans-4-(4-Isopropyl-piperazine-1-carbonyl)-cyclohexyl]-4-methanesulfonyl-benzenesulfonamide | trans-(4-amino-cyclohexyl)-(4-isopropyl-piperazin-1-yl)-methanone (intermediate 1) and 4-methanesulfonyl-benzenesulfonyl chloride (commercially available) | 472.2 |
| 49 | 429 | 6-chloro-pyridine-3-sulfonic acid [trans-4-(4-isopropyl-piperazine-1-carbonyl)-cyclohexyl]-amide | trans-(4-amino-cyclohexyl)-(4-isopropyl-piperazin-1-yl)-methanone (intermediate 1) and 6-chloro-pyridine-3-sulfonyl chloride (commercially available) | 429.1 |

Example 50

N-[trans-4-(4-Isopropyl-piperazine-1-carbonyl)-cyclohexyl]-2,N-dimethyl-benzenesulfonamide A mixture of 41 mg (0.1 mmol) N-{trans-4-[(4-isopropylpiperazin-1-yl)carbonyl]cyclohexyl}-2-methylbenzenesulfonamide (example 4), 72 mg (0.3 mmol) cyanomethylene tri-n-butylphosphorane and 32 mg (1 mmol) methanol in 2 mL toluene was heated for 16 h to 110° C. After evaporation methanol and DMF were added and the mixture was subjected to preparative HPLC purification on reversed phase eluting with a gradient of acetonitrile/water (0.1% NEt$_3$). The combined product fractions were evaporated to dryness to yield 12.4 mg (29%) of the title compound. MS (m/e): 422.2 (MH$^+$).

According to the procedure described for example 50 further piperazinyl-carbonyl-cyclohexyl sulfonamide derivatives have been synthesized from their respective starting materials mentioned in table 2. Table 2 comprises examples 51 to 84.

TABLE 2

| Ex. No. | MW | Name | Starting materials | MW found (MH+) |
|---|---|---|---|---|
| 51 | 443.6 | 2,4-difluoro-N-[trans-4-(4-isopropyl-piperazine-1-carbonyl)-cyclohexyl]-N-methyl-benzenesulfonamide | 2,4-difluoro-N-{trans-4-[(4-isopropylpiperazin-1-yl)carbonyl]cyclohexyl}-benzenesulfonamide (Example 12) and methanol (commercially available) | 444.3 |
| 52 | 449.7 | N-[trans-4-(4-isopropyl-piperazine-1-carbonyl)-cyclohexyl]-2,4,6,N-tetramethyl-benzenesulfonamide | N-{trans-4-[(4-isopropyl-piperazin-1-yl)carbonyl]-cyclohexyl}-2,4,6-trimethyl-benzenesulfonamide (example 13) and methanol (commercially available) | 450.3 |
| 53 | 460 | 3-chloro-4-fluoro-N-[trans-4-(4-isopropyl-piperazine-1-carbonyl)-cyclohexyl]-N-methyl-benzenesulfonamide | 3-chloro-4-fluoro-N-{trans-4-[(4-isopropylpiperazin-1-yl)carbonyl]cyclohexyl}-benzenesulfonamide (example 14) and methanol (commercially available) | 460.2 |
| 54 | 475.6 | N-[trans-4-(4-isopropyl-piperazine-1-carbonyl)-cyclohexyl]-N-methyl-4-trifluoromethyl-benzenesulfonamide | N-{trans-4-[(4-isopropyl-piperazin-1-yl)carbonyl]-cyclohexyl}-4-(trifluoromethyl)benzene-sulfonamide (example 18) and methanol (commercially available) | 476.2 |
| 55 | 476.5 | 3,4-dichloro-N-[trans-4-(4-isopropyl-piperazine-1-carbonyl)-cyclohexyl]-N-methyl-benzenesulfonamide | 3,4-dichloro-N-{trans-4-[(4-isopropylpiperazin-1-yl)carbonyl]cyclohexyl}-benzenesulfonamide (example 20) and methanol (commercially available) | 476.2 |
| 56 | 432.6 | 2-cyano-N-[trans-4-(4-isopropyl-piperazine-1-carbonyl)-cyclohexyl]-N-methyl-benzenesulfonamide | 2-cyano-N-{trans-4-[(4-isopropylpiperazin-1-yl)carbonyl]cyclohexyl}-benzenesulfonamide (example 34) and | 433.3 |

TABLE 2-continued

| Ex. No. | MW | Name | Starting materials | MW found (MH+) |
|---|---|---|---|---|
| 57 | 491.6 | N-[trans-4-(4-isopropyl-piperazine-1-carbonyl)-cyclohexyl]-N-methyl-4-trifluoromethoxy-benzenesulfonamide | N-{trans-4-[(4-isopropyl-piperazin-1-yl)carbonyl]-cyclohexyl}-4-(trifluoromethoxy)-benzenesulfonamide (example 35) and methanol (commercially available) | 492.4 |
| 58 | 432.6 | 4-cyano-N-[trans-4-(4-isopropyl-piperazine-1-carbonyl)-cyclohexyl]-N-methyl-benzenesulfonamide | 4-cyano-N-{trans-4-[(4-isopropylpiperazin-1-yl)carbonyl]cyclohexyl}-benzenesulfonamide (example 7) and methanol (commercially available) | 433.3 |
| 59 | 450.6 | 3-cyano-4-fluoro-N-[trans-4-(4-isopropyl-piperazine-1-carbonyl)-cyclohexyl]-N-methyl-benzenesulfonamide | 3-cyano-4-fluoro-N-[trans-4-(4-isopropyl-piperazine-1-carbonyl)-cyclohexyl]-benzenesulfonamide (example 46) and methanol (commercially available) | 451.3 |
| 60 | 449.7 | N-isopropyl-N-[trans-4-(4-isopropyl-piperazine-1-carbonyl)-cyclohexyl]-2-methyl-benzenesulfonamide | N-{trans-4-[(4-isopropyl-piperazin-1-yl)carbonyl]-cyclohexyl}-2-methyl-benzenesulfonamide (Example 4) and 2-propanol (commercially available) | 450.3 |
| 61 | 465.7 | N-isopropyl-N-[trans-4-(4-isopropyl-piperazine-1-carbonyl)-cyclohexyl]-4-methoxy-benzenesulfonamide | N-{trans-4-[(4-isopropylpiperazin-1-yl)carbonyl]cyclohexyl}-4-methoxybenzene-sulfonamide (example 8) and 2-propanol (commercially available) | 466.3 |
| 62 | 471.6 | 2,4-difluoro-N-isopropyl-N-[trans-4-(4-isopropyl-piperazine-1-carbonyl)-cyclohexyl]-benzenesulfonamide | 2,4-difluoro-N-{trans-4-[(4-isopropylpiperazin-1-yl)carbonyl]cyclohexyl}-benzenesulfonamide (Example 12) and 2-propanol (commercially available) | 472.3 |
| 63 | 477.7 | N-isopropyl-N-[trans-4-(4-isopropyl-piperazine-1-carbonyl)-cyclohexyl]-2,4,6-trimethyl-benzenesulfonamide | N-{trans-4-[(4-isopropyl-piperazin-1-yl)carbonyl]-cyclohexyl}-2,4,6-trimethyl-benzenesulfonamide (example 13) and 2-propanol (commercially available) | 478.3 |
| 64 | 488.1 | 3-chloro-4-fluoro-N-isopropyl-N-[trans-4-(4-isopropyl-piperazine-1-carbonyl)-cyclohexyl]-benzenesulfonamide | 3-chloro-4-fluoro-N-{trans-4-[(4-isopropylpiperazin-1-yl)carbonyl]cyclohexyl}benzenesulfonamide (example 14) and 2-propanol (commercially available) | 488.4 |
| 65 | 503.6 | N-isopropyl-N-[trans-4-(4-isopropyl-piperazine-1-carbonyl)-cyclohexyl]-4-trifluoromethyl-benzenesulfonamide | N-{trans-4-[(4-isopropyl-piperazin-1-yl)carbonyl]-cyclohexyl}-4-(trifluoromethyl)-benzenesulfonamide (example 18) and 2-propanol (commercially available) | 504.3 |
| 66 | 460.6 | 2-cyano-N-isopropyl-N-[trans-4-(4-isopropyl-piperazine-1-carbonyl)-cyclohexyl]-benzenesulfonamide | 2-cyano-N-{trans-4-[(4-isopropylpiperazin-1-yl)carbonyl]cyclohexyl}-benzenesulfonamide (example 34) and 2-propanol (commercially available) | 461.4 |
| 67 | 519.6 | N-isopropyl-N-[trans-4-(4-isopropyl-piperazine-1-carbonyl)-cyclohexyl]-4-trifluoromethoxy-benzenesulfonamide | N-{trans-4-[(4-isopropylpiperazin-1-yl)carbonyl]-cyclohexyl}-4-(trifluoromethoxy)-benzenesulfonamide (example 35) and 2-propanol (commercially available) | 520.3 |
| 68 | 478.6 | 3-cyano-4-fluoro-N-isopropyl-N-[trans-4-(4-isopropyl-piperazine-1-carbonyl)-cyclohexyl]-benzenesulfonamide | 3-cyano-4-fluoro-N-[trans-4-(4-isopropyl-piperazine-1-carbonyl)-cyclohexyl]-benzenesulfonamide (example 46) and 2-propanol (commercially available) | 479.2 |
| 69 | 492.7 | N-(4-{isopropyl-[trans-4-(4-isopropyl-piperazine-1-carbonyl)-cyclohexyl]-sulfamoyl}-phenyl)-acetamide | N-{trans-4-[4-(4-csopropyl-piperazine-1-carbonyl)-cyclohexylsulfamoyl]-phenyl}-acetamide (example 47) and 2-propanol (commercially available) | 493.4 |
| 70 | 471.1 | 6-chloro-pyridine-3-sulfonic acid isopropyl-[trans-4-(4-isopropyl-piperazine-1-carbonyl)-cyclohexyl]-amide | 6-chloro-pyridine-3-sulfonic acid [trans-4-(4-isopropyl-piperazine-1-carbonyl)-cyclohexyl]-amide (example 49) and 2-propanol (commercially available) | 471.3 |
| 71 | 461.7 | N-cyclopropylmethyl-N-[trans-4-(4-isopropyl-piperazine-1-carbonyl)-cyclohexyl]-2-methyl-benzenesulfonamide | N-{trans-4-[(4-isopropyl-piperazin-1-yl)carbonyl]-cyclohexyl}-2-methyl-benzenesulfonamide (Example 4) and cyclopropyl-methanol (commercially available) | 462.4 |
| 72 | 477.7 | N-cyclopropylmethyl-N-[trans-4-(4-isopropyl-piperazine-1-carbonyl)-cyclohexyl]-4-methoxy-benzenesulfonamide | N-{trans-4-[(4-isopropylpiperazin-1-yl)carbonyl]cyclohexyl}-4-methoxybenzene-sulfonamide (example 8) and cyclopropyl-methanol (commercially available) | 478.3 |
| 73 | 483.6 | N-cyclopropylmethyl-2,4-difluoro-N-[trans-4-(4-isopropyl-piperazine-1-carbonyl)-cyclohexyl]-benzenesulfonamide | 2,4-difluoro-N-{trans-4-[(4-isopropylpiperazin-1-yl)carbonyl]cyclohexyl}-benzenesulfonamide (Example 12) and cyclopropyl-methanol (commercially available) | 484.3 |
| 74 | 489.7 | N-cyclopropylmethyl-N-[trans-4-(4-isopropyl-piperazine-1-carbonyl)-cyclohexyl]-2,4,6-trimethyl-benzenesulfonamide | N-{trans-4-[(4-isopropyl-piperazin-1-yl)carbonyl]-cyclohexyl}-2,4,6-trimethyl-benzenesulfonamide (example 13) and | 490.3 |

TABLE 2-continued

| Ex. No. | MW | Name | Starting materials | MW found (MH+) |
|---|---|---|---|---|
| 75 | 500.1 | 3-chloro-N-cyclopropyl-methyl-4-fluoro-N-[trans-4-(4-isopropyl-piperazine-1-carbonyl)-cyclohexyl]-benzenesulfonamide | 3-chloro-4-fluoro-N-{trans-4-[(4-isopropylpiperazin-1-yl)carbonyl]cyclo-hexyl}-benzenesulfonamide (example 14) and cyclopropyl-methanol (commercially available) | 500.2 |
| 76 | 515.6 | N-cyclopropylmethyl-N-[trans-4-(4-isopropyl-piperazine-1-carbonyl)-cyclohexyl]-4-trifluoromethyl-benzenesulfonamide | N-{trans-4-[(4-isopropyl-piperazin-1-yl)carbonyl]-cyclohexyl}-4-(trifluoro-methyl)benzene-sulfonamide (example 18) and cyclopropyl-methanol (commercially available) | 516.3 |
| 77 | 516.5 | 3,4-dichloro-N-cyclopropylmethyl-N-[trans-4-(4-isopropyl-piperazine-1-carbonyl)-cyclohexyl]-benzenesulfonamide | 3,4-dichloro-N-{trans-4-[(4-isopropylpiperazin-1-yl)carbonyl]cyclo-hexyl}-benzenesulfonamide (example 20) and cyclopropyl-methanol (commercially available) | 516.3 |
| 78 | 472.7 | 2-cyano-N-cyclopropyl-methyl-N-[trans-4-(4-isopropyl-piperazine-1-carbonyl)-cyclohexyl]-benzenesulfonamide | 2-cyano-N-{trans-4-[(4-isopropylpiperazin-1-yl)carbonyl]cyclo-hexyl}-benzenesulfonamide (example 34) and cyclopropyl-methanol (commercially available) | 473.2 |
| 79 | 531.6 | N-cyclopropylmethyl-N-[trans-4-(4-isopropyl-piperazine-1-carbonyl)-cyclohexyl]-4-trifluoromethoxy-benzenesulfonamide | N-{trans-4-[(4-isopropyl-piperazin-1-yl)carbonyl]-cyclohexyl}-4-(trifluoro-methoxy)-benzenesulfonamide (example 35) and cyclopropyl-methanol (commercially available) | 532.3 |
| 80 | 489.7 | 4-acetyl-N-cyclopropyl-methyl-N-[trans-4-(4-isopropyl-piperazine-1-carbonyl)-cyclohexyl]-benzenesulfonamide | 4-acetyl-N-{trans-4-[(4-isopropylpiperazin-1-yl)carbonyl]cyclo-hexyl}-benzenesulfonamide (example 41) and cyclopropyl-methanol (commercially available) | 490.3 |
| 81 | 472.7 | 4-cyano-N-cyclopropyl-methyl-N-[trans-4-(4-isopropyl-piperazine-1-carbonyl)-cyclohexyl]-benzenesulfonamide | 4-cyano-N-{trans-4-[(4-isopropylpiperazin-1-yl)carbonyl]cyclo-hexyl}-benzenesulfonamide (example 7) and cyclopropyl-methanol (commercially available) | 473.2 |
| 82 | 490.6 | 3-cyano-N-cyclopropyl-methyl-4-fluoro-N-[trans-4-(4-isopropyl-piperazine-1-carbonyl)-cyclohexyl]-benzenesulfonamide | 3-cyano-4-fluoro-N-[trans-4-(4-isopropyl-piperazine-1-carbonyl)-cyclohexyl]-benzenesulfonamide (example 46) and cyclopropyl-methanol (commercially available) | 491.3 |
| 83 | 525.7 | N-cyclopropylmethyl-N-[trans-4-(4-isopropyl-piperazine-1-carbonyl)-cyclohexyl]-4-methanesulfonyl-benzenesulfonamide | N-[trans-4-(4-isopropyl-piperazine-1-carbonyl)-cyclohexyl]-4-methane-sulfonyl-benzenesulfonamide (example 48) and cyclopropyl-methanol (commercially available) | 526.3 |
| 84 | 483.1 | 6-chloro-pyridine-3-sulfonic acid cyclopropyl-methyl-[trans-4-(4-isopropyl-piperazine-1-carbonyl)-cyclohexyl]-amide | 6-chloro-pyridine-3-sulfonic acid [trans-4-(4-isopropyl-piperazine-1-carbonyl)-cyclohexyl]-amide (example 49) and cyclopropyl-methanol (commercially available) | 483.3 |

In analogy to the procedure described for the synthesis of N-{trans-4-[(4-isopropylpiperazin-1-yl)carbonyl]cyclohexyl}propane-1-sulfonamide (example 1) further piperazinyl-carbonyl-cyclohexyl sulfonamide derivatives have been synthesized from their respective starting materials mentioned in table 3. Table 3 comprises examples 85 to 137.

TABLE 3

| No | MW | Name | Starting materials | MW found (MH+) |
|---|---|---|---|---|
| 85 | 433.6 | trans-N-[4-(4-cyclopentyl-piperazine-1-carbonyl)-cyclohexyl]-2-methyl-benzenesulfonamide | trans-(4-amino-cyclohexyl)-(4-cyclopentyl-piperazin-1-yl)-methanone, dihydrochloride (intermediate 3) and 2-methyl-benzenesulfonyl chloride (commercially available) | 434.3 |
| 86 | 455.6 | trans-N-[4-(4-cyclopentyl-piperazine-1-carbonyl)-cyclohexyl]-2,4-difluoro-benzenesulfonamide | trans-(4-amino-cyclohexyl)-(4-cyclopentyl-piperazin-1-yl)-methanone, dihydrochloride (intermediate 3) and 2,4-difluoro-benzenesulfonyl chloride (commercially available) | 456.3 |
| 87 | 472 | trans-3-chloro-N-[4-(4-cyclopentyl-piperazine-1-carbonyl)-cyclohexyl]-4-fluoro-benzenesulfonamide | trans-(4-amino-cyclohexyl)-(4-cyclopentyl-piperazin-1-yl)-methanone, dihydrochloride (intermediate 3) and 3-chloro-4-fluoro-benzenesulfonyl chloride (commercially available) | 472.2 |
| 88 | 487.6 | trans-N-[4-(4-cyclopentyl-piperazine-1-carbonyl)-cyclohexyl]-4-trifluoro-methyl-benzenesulfonamide | trans-(4-amino-cyclohexyl)-(4-cyclopentyl-piperazin-1-yl)-methanone, dihydrochloride (intermediate 3) and 4-trifluoromethyl-benzenesulfonyl chloride (commercially available) | 488.4 |
| 89 | 503.6 | trans-N-[4-(4-cyclopentyl-piperazine-1-carbonyl)-cyclohexyl]-4-trifluoromethoxy-benzenesulfonamide | trans-(4-amino-cyclohexyl)-(4-cyclopentyl-piperazin-1-yl)-methanone, dihydrochloride (intermediate 3) and 4-trifluoromethoxy-benzenesulfonyl chloride (commercially available) | 504.2 |
| 90 | 461.6 | trans-4-acetyl-N-[4-(4-cyclopentyl-piperazine-1- | trans-(4-amino-cyclohexyl)-(4-cyclopentyl-piperazin- | 462.4 |

TABLE 3-continued

| No | MW | Name | Starting materials | MW found (MH+) |
|---|---|---|---|---|
| | | carbonyl)-cyclohexyl]-benzenesulfonamide | 1-yl)-methanone, dihydrochloride (intermediate 3) and 4-acetyl-benzenesulfonyl chloride (commercially available) | |
| 91 | 444.6 | trans-4-cyano-N-[4-(4-cyclopentyl-piperazine-1-carbonyl)-cyclohexyl]-benzenesulfonamide | trans-(4-amino-cyclohexyl)-(4-cyclopentyl-piperazin-1-yl)-methanone, dihydrochloride (intermediate 3) and 4-cyano-benzenesulfonyl chloride (commercially available) | 445.3 |
| 92 | 462.6 | trans-3-cyano-N-[4-(4-cyclopentyl-piperazine-1-carbonyl)-cyclohexyl]-4-fluoro-benzenesulfonamide | trans-(4-amino-cyclohexyl)-(4-cyclopentyl-piperazin-1-yl)-methanone, dihydrochloride (intermediate 3) and 3-cyano-4-fluoro-benzenesulfonyl chloride (commercially available) | 463.2 |
| 93 | 497.7 | trans-N-[4-(4-cyclopentyl-piperazine-1-carbonyl)-cyclohexyl]-4-methanesulfonyl-benzenesulfonamide | trans-(4-amino-cyclohexyl)-(4-cyclopentyl-piperazin-1-yl)-methanone, dihydrochloride (intermediate 3) and 4-methanesulfonyl-benzenesulfonyl chloride (commercially available) | 498.3 |
| 94 | 455 | trans-6-chloro-pyridine-3-sulfonic acid [4-(4-cyclopentyl-piperazine-1-carbonyl)-cyclohexyl]-amide | trans-(4-amino-cyclohexyl)-(4-cyclopentyl-piperazin-1-yl)-methanone, dihydrochloride (intermediate 3) and 6-chloro-pyridine-3-sulfonyl chloride (commercially available) | 455.2 |
| 95 | 419.6 | trans-N-[4-(4-cyclobutyl-piperazine-1-carbonyl)-cyclohexyl]-2-methyl-benzenesulfonamide | trans-(4-amino-cyclohexyl)-(4-cyclobutyl-piperazin-1-yl)-methanone, dihydrochloride (intermediate 4) and 2-methyl-benzenesulfonyl chloride (commercially available) | 420.3 |
| 96 | 441.5 | trans-N-[4-(4-cyclobutyl-piperazine-1-carbonyl)-cyclohexyl]-2,4-difluoro-benzenesulfonamide | trans-(4-amino-cyclohexyl)-(4-cyclobutyl-piperazin-1-yl)-methanone, dihydrochloride (intermediate 4) and 2,4-difluoro-benzenesulfonyl chloride (commercially available) | 442.3 |
| 97 | 458 | trans-3-chloro-N-[4-(4-cyclobutyl-piperazine-1-carbonyl)-cyclohexyl]-4-fluoro-benzenesulfonamide | trans-(4-amino-cyclohexyl)-(4-cyclobutyl-piperazin-1-yl)-methanone, dihydrochloride (intermediate 4) and 3-chloro-4-fluoro-benzenesulfonyl chloride (commercially available) | 458.3 |
| 98 | 473.6 | trans-N-[4-(4-cyclobutyl-piperazine-1-carbonyl)-cyclohexyl]-4-trifluoromethyl-benzenesulfonamide | trans-(4-amino-cyclohexyl)-(4-cyclobutyl-piperazin-1-yl)-methanone, dihydrochloride (intermediate 4) and 4-trifluoromethyl-benzenesulfonyl chloride (commercially available) | 474.1 |
| 99 | 430.6 | trans-2-cyano-N-[4-(4-cyclobutyl-piperazine-1-carbonyl)-cyclohexyl]-benzenesulfonamide | trans-(4-amino-cyclohexyl)-(4-cyclobutyl-piperazin-1-yl)-methanone, dihydrochloride (intermediate 4) and 2-cyano-benzenesulfonyl chloride (commercially available) | 431.3 |
| 100 | 489.6 | trans-N-[4-(4-cyclobutyl-piperazine-1-carbonyl)-cyclohexyl]-4-trifluoromethoxy-benzenesulfonamide | trans-(4-amino-cyclohexyl)-(4-cyclobutyl-piperazin-1-yl)-methanone, dihydrochloride (intermediate 4) and 4-trifluoromethoxy-benzenesulfonyl chloride (commercially available) | 490.2 |
| 101 | 447.6 | trans-4-acetyl-N-[4-(4-cyclobutyl-piperazine-1-carbonyl)-cyclohexyl]-benzenesulfonamide | trans-(4-amino-cyclohexyl)-(4-cyclobutyl-piperazin-1-yl)-methanone, dihydrochloride (intermediate 4) and 4-acetyl-benzenesulfonyl chloride (commercially available) | 448.2 |
| 102 | 430.6 | trans-4-cyano-N-[4-(4-cyclobutyl-piperazine-1-carbonyl)-cyclohexyl]-benzenesulfonamide | trans-(4-amino-cyclohexyl)-(4-cyclobutyl-piperazin-1-yl)-methanone, dihydrochloride (intermediate 4) and 4-cyano-benzenesulfonyl chloride (commercially available) | 431.4 |
| 103 | 448.6 | trans-3-cyano-N-[4-(4-cyclobutyl-piperazine-1-carbonyl)-cyclohexyl]-4-fluoro-benzenesulfonamide | trans-(4-amino-cyclohexyl)-(4-cyclobutyl-piperazin-1-yl)-methanone, dihydrochloride (intermediate 4) and 3-cyano-4-fluoro-benzenesulfonyl chloride (commercially available) | 449.1 |
| 104 | 462.6 | trans-N-{4-[4-(4-cyclo-butyl-piperazine-1-carbonyl)-cyclohexyl-sulfamoyl]-phenyl}-acetamide | trans-(4-amino-cyclohexyl)-(4-cyclobutyl-piperazin-1-yl)-methanone, dihydrochloride (intermediate 4) and 4-acetylamino-benzene-sulfonyl chloride (commercially available) | 463.4 |
| 105 | 483.6 | trans-N-[4-(4-cyclobutyl-piperazine-1-carbonyl)-cyclohexyl]-4-methane-sulfonyl-benzenesulfon-amide | trans-(4-amino-cyclohexyl)-(4-cyclobutyl-piperazin-1-yl)-methanone, dihydrochloride (intermediate 4) and 4-methanesulfonyl-benzenesulfonyl chloride (commercially available) | 484.4 |
| 106 | 441 | trans-6-chloro-pyridine-3-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 6-chloro-pyridine-3-sulfonyl chloride (commercially available) | 441.1 |

TABLE 3-continued

| No | MW | Name | Starting materials | MW found (MH+) |
|---|---|---|---|---|
| 107 | 421.6 | trans-N-[4-(4-tert-butyl-piperazine-1-carbonyl)-cyclohexyl]-2-methyl-benzenesulfonamide | trans-(4-amino-cyclohexyl)-(4-tert-butyl-piperazin-1-yl)-methanone, dihydrochloride (intermediate 5) and 2-methyl-benzenesulfonyl chloride (commercially available) | 422.4 |
| 108 | 460.01 | trans-N-[4-(4-tert-butyl-piperazine-1-carbonyl)-cyclohexyl]-3-chloro-4-fluoro-benzenesulfonamide | trans-(4-amino-cyclohexyl)-(4-tert-butyl-piperazin-1-yl)-methanone, dihydrochloride (intermediate 5) and 3-chloro-4-fluoro-benzenesulfonyl chloride (commercially available) | 460.3 |
| 109 | 491.57 | trans-N-[4-(4-tert-butyl-piperazine-1-carbonyl)-cyclohexyl]-4-trifluoromethoxy-benzenesulfonamide | trans-(4-amino-cyclohexyl)-(4-tert-butyl-piperazin-1-yl)-methanone, dihydrochloride (intermediate 5) and 4-trifluoromethoxy-benzenesulfonyl chloride (commercially available) | 492.4 |
| 110 | 432.59 | trans-N-[4-(4-tert-butyl-piperazine-1-carbonyl)-cyclohexyl]-4-cyano-benzenesulfonamide | trans-(4-amino-cyclohexyl)-(4-tert-butyl-piperazin-1-yl)-methanone, dihydrochloride (intermediate 5) and 4-cyano-benzenesulfonyl chloride (commercially available) | 433.3 |
| 111 | 399.6 | trans-thiophene-2-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and thiophene-2-sulfonyl chloride (commercially available) | 400.2 |
| 112 | 412.6 | trans-3,5-dimethyl-isoxazole-4-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and 3,5-dimethyl-isoxazole-4-sulfonyl chloride (commercially available) | 413.2 |
| 113 | 428.6 | trans-2,4-dimethyl-thiazole-5-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and 2,4-dimethyl-thiazole-5-sulfonyl chloride (commercially available) | 429.3 |
| 114 | 434 | trans-5-chloro-thiophene-2-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and 5-chloro-thiophene-2-sulfonyl chloride (commercially available) | 434.1 |
| 115 | 446 | trans-5-chloro-1,3-dimethyl-1H-pyrazole-4-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and 5-chloro-1,3-dimethyl-1H-pyrazole-4-sulfonyl chloride (commercially available) | 446 |
| 116 | 507.9 | trans-5-bromo-6-chloro-pyridine-3-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and 5-bromo-6-chloro-pyridine-3-sulfonyl chloride (commercially available) | 475 |
| 117 | 512.9 | trans-3-bromo-5-chloro-thiophene-2-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and 3-bromo-5-chloro-thiophene-2-sulfonyl chloride (commercially available) | 514 |
| 118 | 512.9 | trans-4-bromo-5-chloro-thiophene-2-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and 4-bromo-5-chloro-thiophene-2-sulfonyl chloride (commercially available) | 512 |
| 119 | 473.4 | trans-5-bromo-pyridine-3-sulfonic acid [4-(4-isopropyl-piperazine-1-carbonyl)-cyclohexyl]-amide | trans-(4-amino-cyclohexyl)-(4-isopropyl-piperazin-1-yl)-methanone, dihydrochloride (intermediate 1) and 5-bromo-pyridine-3-sulfonyl chloride (commercially available) | 509.2 |
| 120 | 425.6 | trans-thiophene-2-sulfonic acid [4-(4-cyclopentyl-piperazine-1-carbonyl)-cyclohexyl]-amide | trans-(4-amino-cyclohexyl)-(4-cyclopentyl-piperazin-1-yl)-methanone, dihydrochloride (intermediate 3) and thiophene-2-sulfonyl chloride (commercially available) | 426.1 |
| 121 | 438.6 | trans-3,5-dimethyl-isoxazole-4-sulfonic acid [4-(4-cyclopentyl-piperazine-1-carbonyl)-cyclohexyl]-amide | trans-(4-amino-cyclohexyl)-(4-cyclopentyl-piperazin-1-yl)-methanone, dihydrochloride (intermediate 3) and 3,5-dimethyl-isoxazole-4-sulfonyl chloride (commercially available) | 439.2 |
| 122 | 460.1 | trans-5-chloro-thiophene-2-sulfonic acid [4-(4-cyclopentyl-piperazine-1-carbonyl)-cyclohexyl]-amide | trans-(4-amino-cyclohexyl)-(4-cyclopentyl-piperazin-1-yl)-methanone, dihydrochloride (intermediate 3) and 5-chloro-thiophene-2-sulfonyl chloride (commercially available) | 460.2 |
| 123 | 472.1 | trans-5-chloro-1,3-dimethyl-1H-pyrazole-4-sulfonic acid [4-(4-cyclopentyl-piperazine-1-carbonyl)-cyclohexyl]-amide | trans-(4-amino-cyclohexyl)-(4-cyclopentyl-piperazin-1-yl)-methanone, dihydrochloride | 472.1 |

TABLE 3-continued

| No | MW | Name | Starting materials | MW found (MH+) |
|---|---|---|---|---|
| | | piperazine-1-carbonyl)-cyclohexyl]-amide | dihydrochloride (intermediate 3) and 5-chloro-1,3-dimethyl-1H-pyrazole-4-sulfonyl chloride (commercially available) | |
| 124 | 539 | trans-4-bromo-5-chloro-thiophene-2-sulfonic acid [4-(4-cyclopentyl-piperazine-1-carbonyl)-cyclohexyl]-amide | trans-(4-amino-cyclohexyl)-(4-cyclopentyl-piperazin-1-yl)-methanone, dihydrochloride (intermediate 3) and 4-bromo-5-chloro-thiophene-2-sulfonyl chloride (commercially available) | 540.2 |
| 125 | 411.6 | trans-thiophene-2-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and thiophene-2-sulfonyl chloride (commercially available) | 412.1 |
| 126 | 423.6 | trans-2,3-dimethyl-3H-imidazole-4-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 2,3-dimethyl-3H-imidazole-4-sulfonyl chloride (commercially available) | 424.2 |
| 127 | 424.6 | trans-3,5-dimethyl-isoxazole-4-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 3,5-dimethyl-isoxazole-4-sulfonyl chloride (commercially available) | 425.2 |
| 128 | 440.6 | trans-2,4-dimethyl-thiazole-5-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 2,4-dimethyl-thiazole-5-sulfonyl chloride (commercially available) | 441.2 |
| 129 | 446 | trans-5-chloro-thiophene-2-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 5-chloro-thiophene-2-sulfonyl chloride (commercially available) | 446 |
| 130 | 458 | trans-5-chloro-1,3-dimethyl-1H-pyrazole-4-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 5-chloro-1,3-dimethyl-1H-pyrazole-4-sulfonyl chloride (commercially available) | 458.2 |
| 131 | 519.9 | trans-5-bromo-6-chloro-pyridine-3-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 5-bromo-6-chloro-pyridine-3-sulfonyl chloride (commercially available) | 487.1 |
| 132 | 524.9 | trans-3-bromo-5-chloro-thiophene-2-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 3-bromo-5-chloro-thiophene-2-sulfonyl chloride (commercially available) | 525.9 |
| 133 | 524.9 | trans-4-bromo-5-chloro-thiophene-2-sulfonic acid [4-(4-cyclobutyl-piperazine-1-carbonyl)-cyclohexyl]-amide | trans-(4-amino-cyclohexyl)-(4-cyclobutyl-piperazin-1-yl)-methanone, dihydrochloride (intermediate 4) and 4-bromo-5-chloro-thiophene-2-sulfonyl chloride (commercially available) | 525.9 |
| 134 | 413.6 | trans-thiophene-2-sulfonic acid [4-(4-tert-butyl-piperazine-1-carbonyl)-cyclohexyl]-amide | trans-(4-amino-cyclohexyl)-(4-tert-butyl-piperazin-1-yl)-methanone, dihydrochloride (intermediate 5) and thiophene-2-sulfonyl chloride (commercially available) | 414.2 |
| 135 | 426.6 | trans-3,5-dimethyl-isoxazole-4-sulfonic acid [4-(4-tert-butyl-piperazine-1-carbonyl)-cyclohexyl]-amide | trans-(4-amino-cyclohexyl)-(4-tert-butyl-piperazin-1-yl)-methanone, dihydrochloride (intermediate 5) and 3,5-dimethyl-isoxazole-4-sulfonyl chloride (commercially available) | 427.2 |
| 136 | 448 | trans-5-chloro-thiophene-2-sulfonic acid [4-(4-tert-butyl-piperazine-1-carbonyl)-cyclohexyl]-amide | trans-(4-amino-cyclohexyl)-(4-tert-butyl-piperazin-1-yl)-methanone, dihydrochloride (intermediate 5) and 5-chloro-thiophene-2-sulfonyl chloride (commercially available) | 448 |
| 137 | 526.9 | trans-3-bromo-5-chloro-thiophene-2-sulfonic acid [4-(4-tert-butyl-piperazine-1-carbonyl)-cyclohexyl]-amide | trans-(4-amino-cyclohexyl)-(4-tert-butyl-piperazin-1-yl)-methanone, dihydrochloride (intermediate 5) and 3-bromo-5-chloro-thiophene-2-sulfonyl chloride (commercially available) | 527.9 |

In analogy to the procedure described for the synthesis of N-[trans-4-(4-isopropyl-piperazine-1-carbonyl)-cyclohexyl]-2,N-dimethyl-benzenesulfonamide (example 50) further piperazinyl-carbonyl-cyclohexyl sulfonamide derivatives have been synthesized from their respective starting materials mentioned in table 4. Table 4 comprises examples 138 to 162.

TABLE 4

| No | MW | Name | Starting materials | MW found (MH+) |
|---|---|---|---|---|
| 138 | 489.6 | trans-N-[4-(4-isopropyl-piperazine-1-carbonyl)-cyclohexyl]-2-methyl-N-(2,2,2-trifluoro-ethyl)-benzenesulfonamide | N-{trans-4-[(4-isopropylpiperazin-1-yl)carbonyl]cyclohexyl}-2-methylbenzenesulfonamide (example 4) and 2,2,2-trifluoro-ethanol (commercially available) | 490.3 |
| 139 | 505.6 | trans-N-[4-(4-isopropyl-piperazine-1-carbonyl)-cyclohexyl]-4-methoxy-N-(2,2,2-trifluoro-ethyl)-benzenesulfonamide | N-{trans-4-[(4-isopropylpiperazin-1-yl)carbonyl]cyclohexyl}-4-methoxybenzenesulfonamide (example 8) and 2,2,2-trifluoro-ethanol (commercially available) | 506.2 |
| 140 | 511.6 | trans-2,4-difluoro-N-[4-(4-isopropyl-piperazine-1-carbonyl)-cyclohexyl]-N-(2,2,2-trifluoro-ethyl)-benzenesulfonamide | 2,4-difluoro-N-{trans-4-[(4-isopropylpiperazin-1-yl)carbonyl]cyclohexyl}benzenesulfonamide (example 12) and 2,2,2-trifluoro-ethanol (commercially available) | 512.2 |
| 141 | 517.7 | trans-N-[4-(4-isopropyl-piperazine-1-carbonyl)-cyclohexyl]-2,4,6-trimethyl-N-(2,2,2-trifluoro-ethyl)-benzenesulfonamide | N-{trans-4-[(4-isopropylpiperazin-1-yl)carbonyl]cyclohexyl}-2,4,6-trimethylbenzene-sulfonamide (example 13) and 2,2,2-trifluoro-ethanol (commercially available) | 518.2 |
| 142 | 528 | trans-3-chloro-4-fluoro-N-[4-(4-isopropyl-piperazine-1-carbonyl)-cyclohexyl]-N-(2,2,2-trifluoro-ethyl)-benzenesulfonamide | 3-chloro-4-fluoro-N-{trans-4-[(4-isopropylpiperazin-1-yl)carbonyl]cyclohexyl}-benzenesulfonamide (example 14) and 2,2,2-trifluoro-ethanol (commercially available) | 528 |
| 143 | 543.6 | trans-N-[4-(4-isopropyl-piperazine-1-carbonyl)-cyclohexyl]-N-(2,2,2-trifluoro-ethyl)-4-trifluoromethyl-benzenesulfonamide | N-{trans-4-[(4-isopropylpiperazin-1-yl)carbonyl]cyclohexyl}-4-(trifluoromethyl)-benzenesulfonamide (example 18) and 2,2,2-trifluoro-ethanol (commercially available) | 544.2 |
| 144 | 544.5 | trans-3,4-dichloro-N-[4-(4-isopropyl-piperazine-1-carbonyl)-cyclohexyl]-N-(2,2,2-trifluoro-ethyl)-benzenesulfonamide | 3,4-dichloro-N-{trans-4-[(4-isopropylpiperazin-1-yl)carbonyl]cyclohexyl}-benzenesulfonamide (example 20) and 2,2,2-trifluoro-ethanol (commercially available) | 544.2 |
| 145 | 500.6 | trans-2-cyano-N-[4-(4-isopropyl-piperazine-1-carbonyl)-cyclohexyl]-N-(2,2,2-trifluoro-ethyl)-benzenesulfonamide | 2-cyano-N-{trans-4-[(4-isopropylpiperazin-1-yl)carbonyl]cyclohexyl}-benzenesulfonamide (example 34) and 2,2,2-trifluoro-ethanol (commercially available) | 501.1 |
| 146 | 559.6 | trans-N-[4-(4-isopropyl-piperazine-1-carbonyl)-cyclohexyl]-N-(2,2,2-trifluoro-ethyl)-4-trifluoromethoxy-benzenesulfonamide | N-{trans-4-[(4-isopropylpiperazin-1-yl)carbonyl]cyclohexyl}-4-(trifluoromethoxy)-benzenesulfonamide (example 35) and 2,2,2-trifluoro-ethanol (commercially available) | 560.3 |
| 147 | 517.6 | trans-4-acetyl-N-[4-(4-isopropyl-piperazine-1-carbonyl)-cyclohexyl]-N-(2,2,2-trifluoro-ethyl)-benzenesulfonamide | 4-acetyl-N-{trans-4-[(4-isopropylpiperazin-1-yl)carbonyl]cyclohexyl}-benzenesulfonamide (example 41) and 2,2,2-trifluoro-ethanol (commercially available) | 518.1 |

TABLE 4-continued

| No | MW | Name | Starting materials | MW found (MH+) |
|---|---|---|---|---|
| 148 | 500.6 | trans-4-cyano-N-[4-(4-isopropyl-piperazine-1-carbonyl)-cyclohexyl]-N-(2,2,2-trifluoro-ethyl)-benzenesulfonamide | 4-cyano-N-{trans-4-[(4-isopropylpiperazin-1-yl)carbonyl]cyclohexyl}-benzenesulfonamide (example 7) and 2,2,2-trifluoro-ethanol (commercially available) | 501.1 |
| 149 | 518.6 | trans-3-cyano-4-fluoro-N-[4-(4-isopropyl-piperazine-1-carbonyl)-cyclohexyl]-N-(2,2,2-trifluoro-ethyl)-benzenesulfonamide | 3-cyano-4-fluoro-N-[trans-4-(4-isopropyl-piperazine-1-carbonyl)-cyclohexyl]-benzenesulfonamide (example 46) and 2,2,2-trifluoro-ethanol (commercially available) | 519.2 |
| 150 | 532.6 | trans-N-{4-[[4-(4-isopropyl-piperazine-1-carbonyl)-cyclohexyl]-(2,2,2-trifluoro-ethyl)-sulfamoyl]-phenyl}-acetamide | N-{trans-4-[4-(4-isopropyl-piperazine-1-carbonyl)-cyclohexylsulfamoyl]-phenyl}-acetamide (example 47) and 2,2,2-trifluoro-ethanol (commercially available) | 533.3 |
| 151 | 511 | trans-6-chloro-pyridine-3-sulfonic acid [4-(4-isopropyl-piperazine-1-carbonyl)-cyclohexyl]-(2,2,2-trifluoro-ethyl)-amide | 6-chloro-pyridine-3-sulfonic acid [trans-4-(4-isopropyl-piperazine-1-carbonyl)-cyclohexyl]-amide (example 49) and 2,2,2-trifluoro-ethanol (commercially available) | 511.2 |
| 152 | 465.7 | trans)-N-[4-(4-isopropyl-piperazine-1-carbonyl)-cyclohexyl]-N-(2-methoxy-ethyl)-2-methyl-benzenesulfonamide | N-{trans-4-[(4-isopropylpiperazin-1-yl)carbonyl]cyclohexyl}-2-methylbenzenesulfonamide (example 4) and 2-methoxy-ethanol (commercially available) | 466.2 |
| 153 | 487.6 | trans-2,4-difluoro-N-[4-(4-isopropyl-piperazine-1-carbonyl)-cyclohexyl]-N-(2-methoxy-ethyl)-benzenesulfonamide | 2,4-difluoro-N-{trans-4-[(4-isopropylpiperazin-1-yl)carbonyl]cyclohexyl}benzenesulfonamide (example 12) and 2-methoxy-ethanol (commercially available) | 488.1 |
| 154 | 493.7 | trans-N-[4-(4-isopropyl-piperazine-1-carbonyl)-cyclohexyl]-N-(2-methoxy-ethyl)-2,4,6-trimethyl-benzenesulfonamide | N-{trans-4-[(4-isopropyl-piperazin-1-yl)carbonyl]-cyclohexyl}-2,4,6-trimethylbenzenesulfonamide (example 13) and 2-methoxy-ethanol (commercially available) | 494.3 |
| 155 | 504.1 | trans-3-chloro-4-fluoro-N-[4-(4-isopropyl-piperazine-1-carbonyl)-cyclohexyl]-N-(2-methoxy-ethyl)-benzenesulfonamide | 3-chloro-4-fluoro-N-{trans-4-[(4-isopropylpiperazin-1-yl)carbonyl]cyclohexyl}-benzenesulfonamide (example 14) and 2-methoxy-ethanol (commercially available) | 504.2 |
| 156 | 519.6 | trans-N-[4-(4-Isopropyl-piperazine-1-carbonyl)-cyclohexyl]-N-(2-methoxy-ethyl)-4-trifluoromethyl-benzenesulfonamide | N-{trans-4-[(4-isopropylpiperazin-1-yl)carbonyl]cyclohexyl}-4-(trifluoromethyl)benzenesulfonamide (example 18) and 2-methoxy-ethanol (commercially available) | 520.3 |
| 157 | 520.5 | trans-3,4-dichloro-N-[4-(4-isopropyl-piperazine-1-carbonyl)-cyclohexyl]-N-(2-methoxy-ethyl)-benzenesulfonamide | 3,4-dichloro-N-{trans-4-[(4-isopropylpiperazin-1-yl)carbonyl]cyclohexyl}benzenesulfonamide (example 20) and 2-methoxy-ethanol (commercially available) | 520.2 |
| 158 | 535.6 | trans-N-[4-(4-isopropyl-piperazine-1-carbonyl)-cyclohexyl]-N-(2-methoxy-ethyl)-4-trifluoromethoxy-benzenesulfonamide | N-{trans-4-[(4-isopropyl-piperazin-1-yl)carbonyl]-cyclohexyl}-4-(trifluoro-methoxy)benzene-sulfonamide (example 35) and 2-methoxy-ethanol (commercially available | 536.3 |

TABLE 4-continued

| No | MW | Name | Starting materials | MW found (MH+) |
|----|------|------|--------------------|----------------|
| 159 | 493.7 | trans-4-acetyl-N-[4-(4-isopropyl-piperazine-1-carbonyl)-cyclohexyl]-N-(2-methoxy-ethyl)-benzenesulfonamide | 4-acetyl-N-{trans-4-[(4-isopropylpiperazin-1-yl)carbonyl]cyclohexyl}benzenesulfonamide (example 41) and 2-methoxy-ethanol (commercially available) | 494.3 |
| 160 | 476.6 | trans-4-cyano-N-[4-(4-isopropyl-piperazine-1-carbonyl)-cyclohexyl]-N-(2-methoxy-ethyl)-benzenesulfonamide | 4-cyano-N-{trans-4-[(4-isopropylpiperazin-1-yl)carbonyl]cyclohexyl}-benzenesulfonamide (example 7) and 2-methoxy-ethanol (commercially available) | 477 |
| 161 | 508.7 | trans-N-{4-[[4-(4-Isopropyl-piperazine-1-carbonyl)-cyclohexyl]-(2-methoxy-ethyl)-sulfamoyl]-phenyl}-acetamide | N-{trans-4-[4-(4-isopropyl-piperazine-1-carbonyl)-cyclohexylsulfamoyl]-phenyl}-acetamide (example 47) and 2-methoxy-ethanol (commercially available) | 509.4 |
| 162 | 487.1 | trans-6-chloro-pyridine-3-sulfonic acid [4-(4-isopropyl-piperazine-1-carbonyl)-cyclohexyl]-(2-methoxy-ethyl)-amide | 6-chloro-pyridine-3-sulfonic acid [trans-4-(4-isopropyl-piperazine-1-carbonyl)-cyclohexyl]-amide (example 49) and 2-methoxy-ethanol (commercially available) | 487.2 |

Example 163 trans-4-Cyano-N-[4-(4-cyclopropylmethyl-piperazine-1-carbonyl)-cyclohexyl]-benzenesulfonamide Step 1: trans-4-(4-Cyano-benzenesulfonylamino)-cyclohexanecarboxylic acid benzyl ester A mixture of 2 g (8.2 mmol) trans-4-tert-butoxycarbonylamino-cyclohexanecarboxylic acid (commercially available), 0.978 g (9.0 mmol) phenyl-methanol (commercially available), 3.16 g (9.8 mmol) O-benzotriazol-1-yl-N,N,N',N'-tetramethyluronium tetrafluoroborate (TBTU) and 1.24 g (12.3 mmol) NEt₃ in 10 mL DMF was stirred at room temperature for 1 h. The mixture was evaporated to dryness and extracted with DCM and Na₂CO₃ aq. The combined organic phases were dried with MgSO₄ and evaporated. The residue was treated with 100 mL 4N HCl in dioxane at room temperature for 4 h. The mixture was evaporated to dryness to yield trans-4-amino-cyclohexanecarboxylic acid benzyl ester (MS (m/e): 360.4 (MH+)) which was used without further purification. 150 mL DCM was added, 2.95 g (14 mmol) 4-cyano-benzenesulfonyl chloride (commercially available) and 6.17 g (61 mmol) NEt₃ and the mixture was stirred at room temperature for 16 h. The mixture was extracted with DCM and 1N HCl aq. and the combined organic phases were evaporated. The residue was recrystallized from methanol to yield 1.9 g (58%) of the title compound. MS (m/e): 397.0 (MH+).

Step 2: 4-Cyano-N-[4-(piperazine-1-carbonyl)-cyclohexyl]-benzenesulfonamide

A mixture of 1.9 g (4.7 mmol) trans-4-(4-cyano-benzenesulfonylamino)-cyclohexanecarboxylic acid benzyl ester and 0.8 g (1.9 mmol) LiOH in a mixture of methanol, THF and water was stirred at room temperature for 2 h. The mixture was evaporated to dryness and 10 mL DMF, 0.7 g (8.1 mmol) piperazine, 2.87 g (8.9 mmol) TBTU and 2.26 g (22 mmol) NEt₃ was added. The mixture was stirred at room temperature for 1 h and evaporated to dryness. The residue was purified by column chromatography on silica obtaining 0.3 g (16%) of the title compound. MS (m/e): 377.1 (MH+).

Step 3: trans-4-Cyano-N-[4-(4-cyclopropylmethyl-piperazine-1-carbonyl)-cyclohexyl]-benzenesulfonamide A mixture of 0.1 g (0.26 mmol) 4-cyano-N-[4-(piperazine-1-carbonyl)-cyclohexyl]-benzenesulfonamide, 0.022 g (0.31 mmol) cyclopropanecarboxaldehyde (commercially available), 0.159 g (2.65 mmol) acetic acid and 0.073 g (0.34 mmol) sodium triacetoxyborohydride in 1 mL THF was stirred at 80° C. for 1 h. The mixture was subjected to purification on preparative HPLC eluting with a gradient formed from acetonitrile and water. Evaporation of the product fractions yielded 3 mg (2.6%) of the title compound. MS (m/e): 431.4 (MH+).

Example 164 trans-4-Cyano-N-{4-[4-(tetrahydro-pyran-4-yl)-piperazine-1-carbonyl]-cyclohexyl}-benzenesulfonamide In analogy to the procedure described for the synthesis of trans-4-cyano-N-[4-(4-cyclopropylmethyl-piperazine-1-carbonyl)-cyclohexyl]-benzenesulfonamide (example 163) the title compound was prepared from 4-cyano-N[4-(piperazine-1-carbonyl)-cyclohexyl]-benzenesulfonamide and tetrahydro-pyran-4-one (commercially available). MS (m/e): 461.3 (MH+).

Example 165

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 166

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 167

Injection solutions can have the following composition:

| | |
| --- | --- |
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 168

Soft gelatin capsules containing the following ingredients can be manufactured in a conventional manner:

Capsule Contents

| | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |

Gelatin Capsule

| | |
| --- | --- |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 169

Sachets containing the following ingredients can be manufactured in a conventional manner:

| | |
| --- | --- |
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound of formula I:

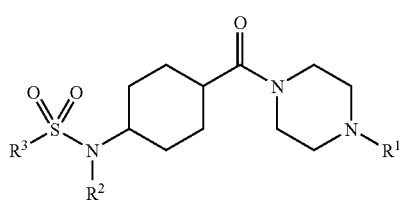

wherein
- $R^1$ is selected from the group consisting of lower alkyl, cycloalkyl, lower cycloalkylalkyl and tetrahydropyranyl;
- $R^2$ is selected from the group consisting of hydrogen, lower alkyl, cycloalkyl, lower cycloalkylalkyl, lower halogenalkyl, lower alkoxyalkyl and lower cyanoalkyl;
- $R^3$ is selected from the group consisting of
  lower alkyl,
  —$(CH_2)_m$-aryl, wherein m is 0, 1 or 2 and wherein the aryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl,
  —$(CH_2)_n$-heteroaryl, wherein n is 0, 1 or 2 and wherein the heteroaryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl, and
  —$NR^4R^5$;
- $R^4$ is selected from the group consisting of hydrogen, lower alkyl, lower halogenalkyl, lower alkoxyalkyl and lower cyanoalkyl;
- $R^5$ is selected from the group consisting of lower alkyl, lower halogenalkyl, lower alkoxyalkyl, lower cyanoalkyl,
  phenyl unsubstituted or substituted with one, two or three groups independently selected from lower alkyl, halogen, lower halogenalkyl, cyano, lower alkoxy, lower alkanoyl, benzoyl, lower halogenalkoxy and lower hydroxyalkyl, and
  lower phenylalkyl wherein the phenyl ring may be unsubstituted or substituted with one or two groups independently selected from lower alkyl, halogen, lower halogenalkyl, cyano, lower alkoxy, lower alkanoyl, benzoyl, lower halogenalkoxy and lower hydroxyalkyl;
  or
- $R^4$ and $R^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group,
  said heterocyclic ring being unsubstituted or substituted by one, two or three groups independently selected from lower alkyl, halogen, halogenalkyl, cyano, hydroxy, lower hydroxyalkyl, lower alkoxy, oxo, phenyl, benzyl, pyridyl and carbamoyl, or
  being condensed with a phenyl ring, said phenyl ring being unsubstituted or substituted by one, two or three groups independently selected from lower alkyl, lower alkoxy and halogen;
  and pharmaceutically acceptable salts thereof.

2. The compound according to claim 1, wherein $R^3$ is lower alkyl.

3. The compound according to claim 1, wherein $R^3$ is $C_3$-$C_8$-alkyl.

4. The compound according to claim 1, wherein $R^3$ is selected from the group consisting of
—$(CH_2)_m$-aryl, wherein m is 0, 1 or 2 and wherein the aryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl, and
—$(CH_2)_n$-heteroaryl, wherein n is 0, 1 or 2 and wherein the heteroaryl ring is unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

5. The compound according to claim 1, wherein $R^3$ is —$(CH_2)_m$-aryl, wherein m is 0, 1 or 2 and wherein the aryl ring is phenyl unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

6. The compound according to claim 1, wherein $R^3$ is phenyl substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

7. The compound according to claim 1, wherein $R^3$ is —$(CH_2)_n$-heteroaryl, wherein n is 0, 1 or 2 and wherein the heteroaryl ring is unsubstituted or substituted with one or two groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

8. The compound according to claim 1, wherein $R^3$ is —$(CH_2)_n$-heteroaryl, wherein n is 0, 1 or 2 and heteroaryl is selected from the group consisting of pyridyl, thienyl, imidazolyl, isoxazolyl, thiazolyl and pyrazolyl, said heteroaryl ring being unsubstituted or substituted with one, two or three groups independently selected from lower alkyl, halogen, lower halogenalkyl, cyano, lower cyanoalkyl, lower alkoxy, lower alkanoyl, benzoyl, lower halogenalkoxy, lower hydroxyalkyl, lower alkanoylamino and lower alkylsulfonyl.

9. The compound according to claim 1, wherein $R^3$ is pyridyl unsubstituted or substituted with halogen.

10. The compound according to claim 1, wherein $R^3$ is —$NR^4R^5$ and $R^4$ and $R^5$ are lower alkyl.

11. The compound according to claim 1, wherein $R^1$ is lower alkyl or cycloalkyl.

12. The compound according to claim 1, wherein $R^1$ is lower alkyl.

13. The compound according to claim 1, wherein $R^1$ is isopropyl or tert-butyl.

14. The compound according to claim 1, wherein $R^1$ is cycloalkyl.

15. The compound according to claim 1, wherein $R^2$ is selected from the group consisting of hydrogen, lower alkyl and lower cycloalkylalkyl.

16. The compound according to claim 1, wherein $R^2$ is hydrogen.

17. The compound according to claim 1, wherein $R^2$ is lower alkyl.

18. The compound according to claim 1, wherein $R^2$ is lower cycloalkylalkyl.

19. The compound according to claim 1, selected from the group consisting of

N-{trans-4-[(4-isopropylpiperazin-1-yl)carbonyl]cyclohexyl}-2-methylbenzene-sulfonamide, 4-cyano-N-{trans-4-[(4-isopropylpiperazin-1-yl)carbonyl]cyclohexyl}benzene-sulfonamide, 4-fluoro-N-{trans-4-[(4-isopropylpiperazin-1-yl)carbonyl]cyclohexyl}-2-methylbenzene-sulfonamide, 1-(3-fluorophenyl)-N-{trans-4-[(4-isopropylpiperazin-1-yl)carbonyl]cyclohexyl}-methanesulfonamide, N-{trans-4-[(4-isopropylpiperazin-1-yl)carbonyl]cyclohexyl}-2,4,6-trimethylbenzene-sulfonamide, 2,4-dichloro-N-{trans-4-[(4-isopropylpiperazin-1-yl)carbonyl]cyclohexyl}benzene-sulfonamide, 2-chloro-N-{trans-4-[(4-isopropylpiperazin-1-yl)carbonyl]cyclohexyl}benzene-sulfonamide, 3-chloro-4-fluoro-N-isopropyl-N-[trans-4-(4-isopropyl-piperazine-1-carbonyl)-cyclohexyl]-benzenesulfonamide, N-cyclopropylmethyl-N-[trans-4-(4-isopropyl-piperazine-1-carbonyl)-cyclohexyl]-2-methyl-benzene-sulfonamide, N-cyclopropylmethyl-N-[trans-4-(4-isopropyl-piperazine-1-carbonyl)-cyclohexyl]-4-methoxy-benzene-sulfonamide, N-cyclopropylmethyl-N-[trans-4-(4-isopropyl-piperazine-1-carbonyl)-cyclohexyl]-2,4,6-trimethyl-benzene-sulfonamide, N-cyclopropylmethyl-N-[trans-4-(4-isopropyl-piperazine-1-carbonyl)-cyclohexyl]-4-trifluoromethoxy-benzenesulfonamide, trans-N-[4-(4-cyclopentyl-piperazine-1-carbonyl)-cyclohexyl]-2-methyl-benzenesulfonamide, trans-4-cyano-N-[4-(4-cyclopentyl-piperazine-1-carbonyl)-cyclohexyl]-benzenesulfonamide, trans-4-cyano-N-[4-(4-cyclobutyl-piperazine-1-carbonyl)-cyclohexyl]-benzenesulfonamide, trans-3-bromo-5-chloro-thiophene-2-sulfonic acid [4-(4-isopropyl-piperazine-1-carbonyl)-cyclohexyl]-amide, trans-3-bromo-5-chloro-thiophene-2-sulfonic acid [4-(4-cyclobutyl-piperazine-1-carbonyl)-cyclohexyl]-amide, trans-N-[4-(4-isopropyl-piperazine-1-carbonyl)-cyclohexyl]-2,4,6-trimethyl-N-(2,2,2-trifluoro-ethyl)-benzenesulfonamide, trans-N-[4-(4-isopropyl-piperazine-1-carbonyl)-cyclohexyl]-N-(2-methoxy-ethyl)-2,4,6-trimethyl-benzene-sulfonamide, and pharmaceutically acceptable salts thereof.

20. A process for the manufacture of a compound according to claim 1, comprising the steps of:
reacting a compound of formula II

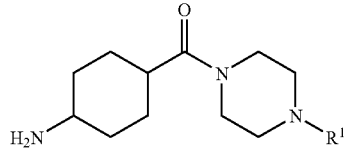

wherein $R^1$ is as defined in claim 1,
with a sulfonyl chloride of formula III

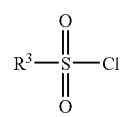

wherein $R^3$ is as defined in claim 1, in the presence of a base to obtain a compound of formula IA

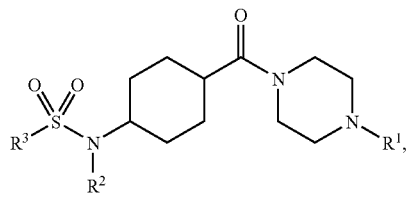

wherein $R^2$ is hydrogen, and optionally alkylating the compound of formula IA to obtain a compound of formula IB

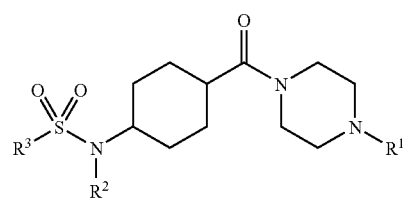

wherein $R^2$ is a group as defined in claim 1 other than hydrogen,
and if desired,
converting the compound obtained into a pharmaceutically acceptable acid addition salt.

21. A pharmaceutical composition, comprising a therapeutically effective amount of a compound according to claim 1 as well as a pharmaceutically acceptable carrier and/or adjuvant.

* * * * *